US011395908B2

(12) United States Patent
Abreu

(10) Patent No.: US 11,395,908 B2
(45) Date of Patent: Jul. 26, 2022

(54) APPARATUS AND METHOD FOR SKIN TREATMENT

(71) Applicant: Brain Tunnelgenix Technologies Corp., Aventura, FL (US)

(72) Inventor: Marcio Marc Abreu, Aventura, FL (US)

(73) Assignee: Brain Tunnelgenix Technologies Corp., Aventura, FL (US)

( * ) Notice: Subject to any disclaimer, the term of this patent is extended or adjusted under 35 U.S.C. 154(b) by 0 days.

(21) Appl. No.: 15/003,564

(22) Filed: Jan. 21, 2016

(65) Prior Publication Data

US 2016/0213905 A1    Jul. 28, 2016

Related U.S. Application Data

(60) Provisional application No. 62/107,270, filed on Jan. 23, 2015.

(51) Int. Cl.
*A61M 35/00* (2006.01)
*A61M 37/00* (2006.01)

(52) U.S. Cl.
CPC ............ *A61M 35/00* (2013.01); *A61M 37/00* (2013.01); *A61M 2037/0007* (2013.01)

(58) Field of Classification Search
CPC .......... A61M 37/00; A61M 2037/0007; A61N 5/025; A61F 2007/0295; A61F 2007/0296; A61F 2007/0298
See application file for complete search history.

(56) References Cited

U.S. PATENT DOCUMENTS

| 6,463,336 | B1 * | 10/2002 | Mawhinney | A61N 1/40 600/14 |
| 9,327,105 | B2 * | 5/2016 | Ramdas | A61M 37/0092 |
| 2001/0037104 | A1 * | 11/2001 | Zhang | A61K 9/0004 604/502 |
| 2002/0169394 | A1 * | 11/2002 | Eppstein | A61B 5/00 600/573 |
| 2003/0040683 | A1 | 2/2003 | Rule et al. | |
| 2003/0149406 | A1 * | 8/2003 | Martineau | A61K 9/7023 604/304 |
| 2003/0219470 | A1 * | 11/2003 | Zhang | A61K 9/0009 424/449 |
| 2004/0073079 | A1 * | 4/2004 | Altshuler | A61B 5/6843 600/1 |

(Continued)

OTHER PUBLICATIONS

Kellogg Jr, Dean L. "In vivo mechanisms of cutaneous vasodilation and vasoconstriction in humans during thermoregulatory challenges." Journal of applied physiology 100.5 (2006): 1709-1718.*

(Continued)

*Primary Examiner* — Adam Marcetich
(74) *Attorney, Agent, or Firm* — Studebaker & Brackett PC

(57) ABSTRACT

Apparatuses and methods configured to provide heat and cold to the skin along with a skin treatment to control rate of skin treatment flow to the skin are described. The disclosed apparatuses and methods include beneficially delaying the transition of skin treatments once skin penetration is achieved to improve the effectiveness of topical treatments to the skin. Accordingly, the disclosed apparatuses and methods are configured to enhance the benefits of topical treatments to the skin.

13 Claims, 22 Drawing Sheets

(56) References Cited

U.S. PATENT DOCUMENTS

| | | | |
|---|---|---|---|
| 2004/0191301 A1* | 9/2004 | Van Duren | A61P 25/34 424/449 |
| 2004/0210280 A1* | 10/2004 | Liedtke | A61F 7/007 607/96 |
| 2004/0219195 A1* | 11/2004 | Hart | A61P 25/00 424/449 |
| 2004/0265353 A1* | 12/2004 | Zhang | A61K 9/0009 424/423 |
| 2005/0096574 A1* | 5/2005 | Wibaux | H05B 3/342 602/2 |
| 2005/0245852 A1* | 11/2005 | Ellefson | A61K 9/703 602/2 |
| 2006/0135911 A1* | 6/2006 | Mittur | A61F 7/007 604/113 |
| 2008/0045879 A1* | 2/2008 | Prausnitz | A61B 5/14514 604/20 |
| 2008/0208162 A1* | 8/2008 | Joshi | A61M 37/00 604/506 |
| 2009/0005745 A1* | 1/2009 | Zhang | A61F 7/034 604/291 |
| 2009/0105605 A1 | 4/2009 | Abreu | |
| 2009/0163984 A1* | 6/2009 | Robinson | A61F 7/02 607/114 |
| 2011/0071603 A1* | 3/2011 | Moore | A61F 7/007 607/96 |
| 2011/0077527 A1 | 3/2011 | Yang et al. | |
| 2011/0086913 A1* | 4/2011 | Zhang | A61F 7/034 514/535 |
| 2011/0218601 A1* | 9/2011 | Uchiyama | A61K 9/0004 607/112 |
| 2011/0264028 A1* | 10/2011 | Ramdas | A61M 5/14248 604/20 |
| 2012/0316624 A1* | 12/2012 | Smith | A61F 7/007 607/99 |
| 2013/0172790 A1* | 7/2013 | Badawi | A61F 7/02 601/15 |
| 2013/0204169 A1* | 8/2013 | Poepperling | A61H 9/0078 601/46 |
| 2013/0281969 A1* | 10/2013 | Blanco | A61M 5/44 604/503 |
| 2014/0046410 A1* | 2/2014 | Wyatt | A61F 7/10 607/104 |
| 2014/0200487 A1* | 7/2014 | Ramdas | G16H 10/60 601/2 |
| 2015/0217098 A1* | 8/2015 | Hicken | A61L 15/44 602/1 |
| 2016/0022478 A1* | 1/2016 | Schaefer | A61F 7/0085 607/104 |

OTHER PUBLICATIONS

Vuksanović, Vesna, Lawrence William Sheppard, and Aneta Stefanovska. "Nonlinear relationship between level of blood flow and skin temperature for different dynamics of temperature change." Biophysical journal 94.10 (2008): L78-L80.*

Notification of Transmittal of the International Search Report and the Written Opinion of the International Searching Authority; PCT/US2016/014346 dated May 17, 2016.

International Preliminary Report on Patentability; PCT/US2016/014346 dated Aug. 3, 2017; 8pp.

* cited by examiner

APPARATUS AND METHOD FOR SKIN TREATMENT

CROSS-REFERENCE TO RELATED APPLICATIONS

This application claims the benefit of priority to U.S. Provisional Patent Application No. 62/107,270, filed on Jan. 23, 2015, which is hereby incorporated by reference in its entirety.

TECHNICAL FIELD

This disclosure relates to apparatuses and methods for application of topical treatments to the skin, particularly human skin.

BACKGROUND

Topical treatments for skin have a long history, extending for at least as long as history has been recorded. These treatments include moisturizers, medications, rejuvenators, hair renewal, vitamins, chemicals, compounds, and various organics, including an array of fruits, vegetables, meat, and processed food.

SUMMARY

Advantages and features of the embodiments of this disclosure will become more apparent from the following detailed description of exemplary embodiments when viewed in conjunction with the accompanying drawings.

DETAILED DESCRIPTION

Applicant investigated thermal effects on the skin to determine whether transdermal permeability could be modified by heat and cold. Applicant unexpectedly discovered that transdermal penetration could be enhanced by an apparatus configured to provide heat and cold to the skin along with a skin treatment. Furthermore, Applicant recognized that such apparatus could beneficially delay the transition of skin treatments once skin penetration was achieved to improve the effectiveness of topical treatments to the skin. Accordingly, the present disclosure provides embodiments of apparatuses and methods configured to enhance the benefits of topical treatments to the skin.

Applicant investigated thermal effects on drug concentration and blood flow in the skin and in adjacent layers. Applicant determined that cosmetics, skin lotions, skin creams, drugs, and the like remained in superficial layers of skin after applying cold, in a specialized manner described herein, using thermoelectric devices and thermally retentive materials, with full description of the devices and materials available in co-pending patent application Ser. No. 14/594,122 by the Applicant filed on Jan. 10, 2015, and incorporated by reference herein in its entirety.

Figure 11:
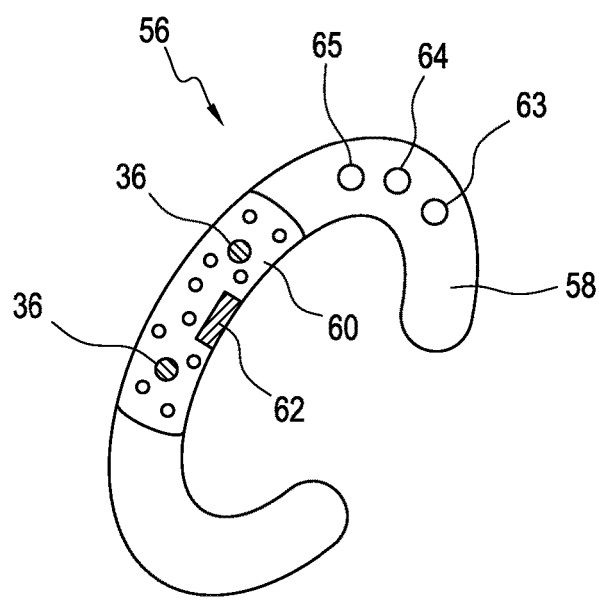
FIG. 11 is a view of a further device for skin treatment in accordance with an exemplary embodiment of the present disclosure.
Figure 14:
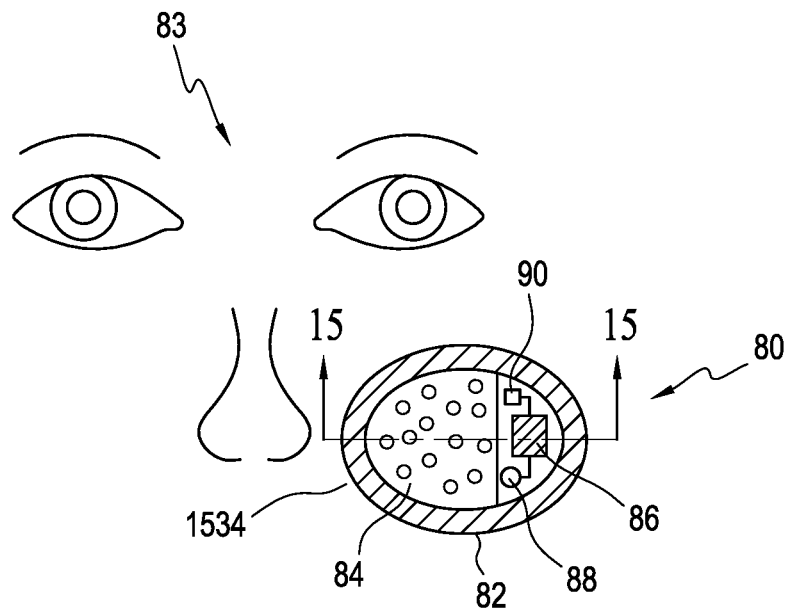
FIG. 14 is a view of the device of FIG. 13A positioned on a face.
Figure 15:
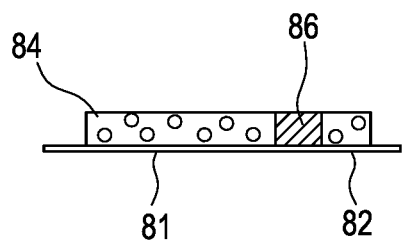
FIG. 15 is a cross-sectional view of the device of FIGS. 13A, 13B, and 14 along lines 15-15 in FIG. 14.

Referring to FIG. 11, an epidermis 1506 and a dermis 1508 are collectively referred to as a superficial skin layer 1520 herein. An area of a skin 1500 where cold is applied is referred to herein as a cold site. Concentrations of a drug 1510, exemplified herein by salicylic acid, and local blood flow in the cold site, were compared to a site with normal skin temperature (referred to herein as a normothermic site). Skin blood flow rate in both the cold site and normothermic site was measured using a laser Doppler perfusion imaging system. Studies also compared plasma concentration of drug 1510 in subjects at the cold site and the normothermic site. An unexpected result was found by the Applicant, which is contrary to the expected result, in which application of cold would cause only minimal amounts of drug to penetrate the skin, and that these minimal amounts of drug would then continue to flow towards subcutaneous fat layer 1512 without any accumulation of drug 1510 in superficial skin layer 1520. However, an unforeseen result was observed by the Applicant, who identified an unexpected effect at the cold site characterized by pooling of drug 1510 in superficial skin layer 1520 of skin 1500. Local distribution of drug 1510 into the cold site significantly increased, and plasma concentration decreased, when compared to a normothermic site. In one exemplary experiment skin blood flow was measured 15 min after application of cold, and every 15 min thereafter for a total of 3 hours. In vitro studies using excised skin were also performed showing that concentrations of drug 1510 in superficial skin layer 1520 of the cold site was about 80% higher when compared to superficial skin layer 1520 of the normothermic site, with cold site skin having drug concentration of 180 nmol per gram of tissue. Plasma concentration at the cold site was about 60% lower when compared to the normothermic site, with the cold site having concentration of about 45 nmol/ml. Skin blood flow in voltages by laser Doppler showed about 50% decrease in superficial skin layer 1520 of the cold site as compared to the normothermic site. The cold effect of a thermoelectric drug device 1530 led to vasoconstriction and to decreased penetration of drug 1510 by reducing a skin blood flow rate and preventing blood vessels in dermis 1508 from absorbing drug 1510, thereby reducing delivery of drug 1510 to systemic circulation, but also pooling of drug 1510 in superficial skin layer 1520 of skin 1500.

Figure 1:
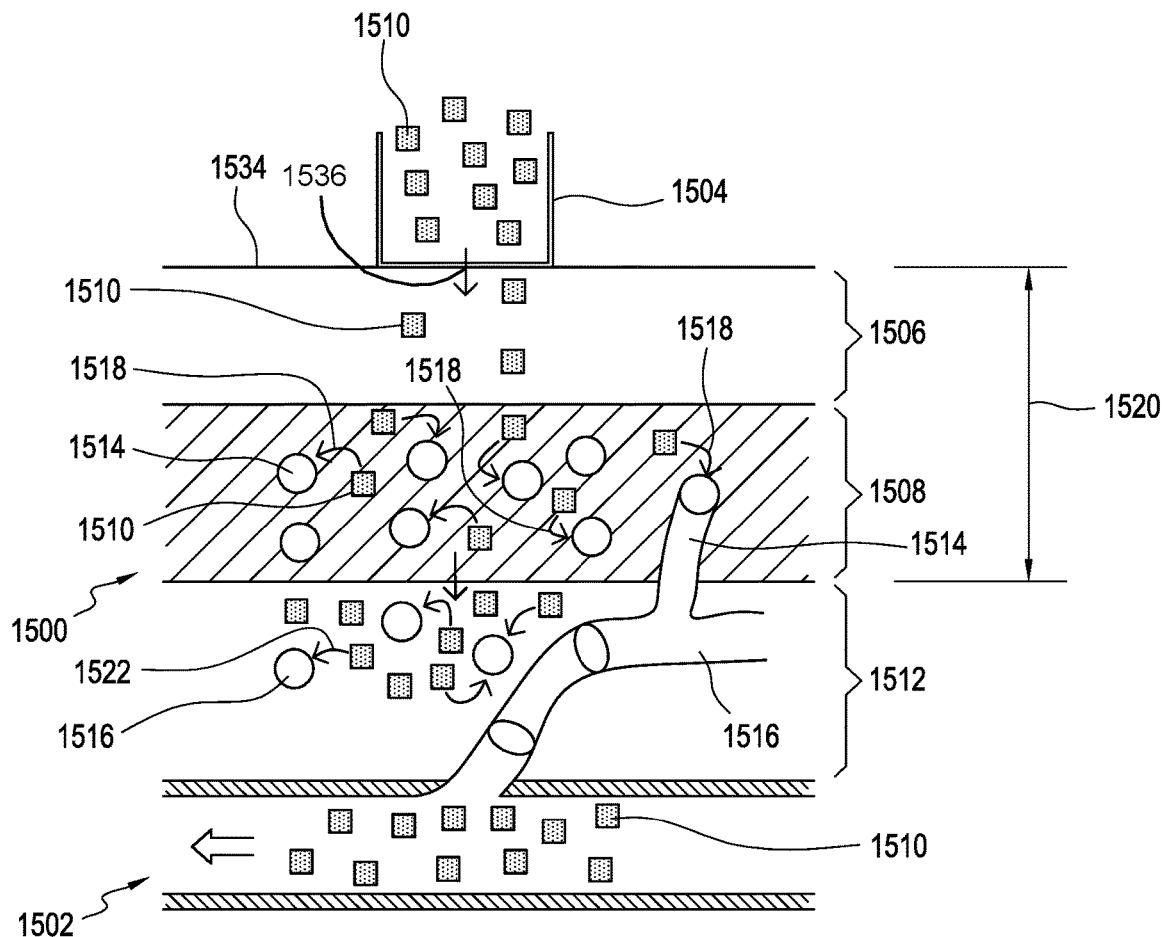
FIG. 1 is a view of a cross-section of skin showing drug transport through skin layers.

FIG. 1 represents skin 1500 with normal temperature (normothermic) and shows a schematic cross-sectional view of skin 1500 with an associated major blood vessel 1502 and a drug reservoir 1504 having drug 1510, drug reservoir 1504 resting on an exterior surface 1534 of skin 1500. Drug 1510, as described herein in this disclosure, may include any chemical compound, cosmetic, beauty products, skin treatment products, and the like including cream, pastes, lotions, solutions, and the like. Skin 1500 includes epidermis 1506, dermis 1508, and subcutaneous fat layer 1512. Drug 1510 flows toward skin 1500, as shown by arrow 1536, going through external surface 1534 and epidermis 1506, reaching dermis 1508, where drug 1510 is absorbed by blood vessels 1514, shown by curved arrows 1518. Drug 1510 continues to flow towards subcutaneous fat layer 1512, where drug 1510 is absorbed by blood vessels 1516, as shown by curved arrows 1522. Drug 1510 then flows to major blood vessel 1502 and into the systemic circulation.

Figure 2:
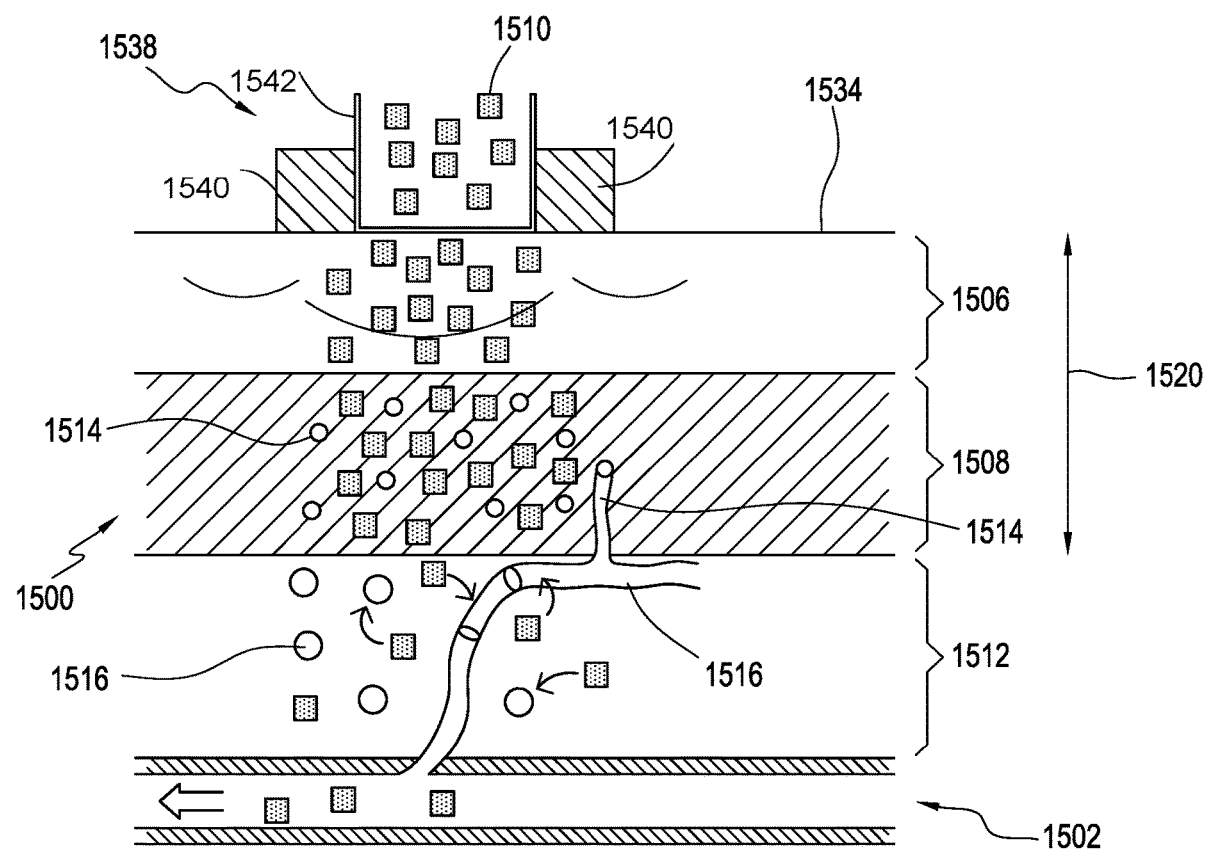
FIG. 2 is a view of a cross-section of skin showing the effect from application of heat and cold in accordance with an exemplary embodiment of the present disclosure.

FIG. 2 represents cold site skin, in which a thermoelectric drug device 1538 of the present disclosure has applied cold to skin 1500, i.e., thermoelectric drug device 1538 is pulling or drawing heat from skin 1500 by the action of one or more thermoelectric devices 1540. Thermoelectric drug device 1538 further includes a drug reservoir 1542, which is positioned between thermoelectric devices 1540. FIG. 2 also shows a schematic cross-sectional view of skin 1500, which has lower temperature than skin 1500 of FIG. 1. Applied cold or removed heat leads to localized vasoconstriction of blood vessels 1514 and 1516, with pooling of drug 1510 in superficial skin layer 1520. Constriction of blood vessels 1514 reduces the amount of drug 1510 taken up by blood vessels 1514, Blood vessels 1516 in subcutaneous fat layer 1512 tend to be less constricted than blood vessels 1514 because of the depth of blood vessels 1516 from exterior surface 1534, and the consequent insulation of blood vessels 1514 from thermoelectric drug device 1538. In addition, the fat that is an integral part of subcutaneous fat layer 1512 has low thermal conductivity, which is similar to oak, thus insulating thermal effect from thermoelectric drug device 1538. The result of removing heat or applying cold to skin 1500 observed in experiments by the Applicant is a pooling of drug 1510 with a large amount of drug 1510 being collected in skin superficial layer 1520.

Figures 3, 4:
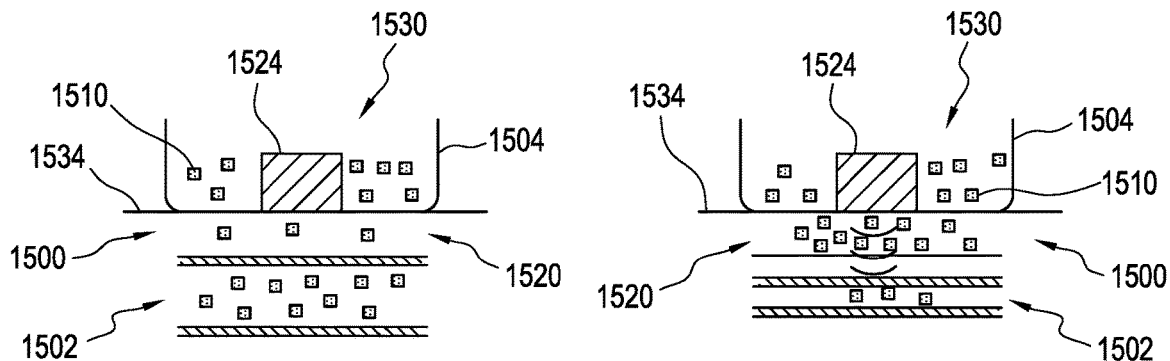
FIG. 3 is a view of drug transport through skin with normal skin temperature.
FIG. 4 is a view of drug transport through skin with heat and cold applied in accordance with an exemplary embodiment of the present disclosure.

FIG. 3 shows a schematic cross-sectional view of skin 1500 in FIG. 1, wherein a thermoelectric device 1524 of thermoelectric drug device 1530 rests on skin 1500, thermoelectric device 1524 being in off position and skin 1500 having normal temperature and blood vessel 1502 having normal dimensions. FIG. 4 shows a schematic cross-sectional view of skin 1500 in FIG. 2, wherein device 1524 rests on skin 1500, device 1524 being activated and removing heat or applying cold to skin 1500, leading blood vessel 1502 to be constricted and causing accumulation of drug 1510 in superficial layer 1520. In one embodiment, a processor or controller generates a thermal cycling process that includes two phases or steps: (1) Phase 1: thermoelectric drug device 1530 is off (corresponding to a normothermic skin site) and said thermoelectric drug device 1530 rests on the normothermic skin, and drug 1510 is delivered to epidermis 1506 by diffusion. (2) Phase 1 Thermoelectric drug device 1530 is on (corresponding to a cold skin site). Once drug 1510 penetrates and is absorbed into epidermis 1506, then said drug 1510 is kept in skin superficial layer 1520 by virtue of the cold effect. It should be understood that the process can include a third phase or step. In Step 3, thermoelectric drug device 1530 applies heat to the skin. Warming up the skin will cause vessels 1516 and 1502 to dilate and increase blood flow, and concentration of drug 1510 in superficial layer 1520 is thereby reduced, causing diffusion of drug 1510 to increase and be absorbed by skin surface 1534. Thus, a drug flow can be created and flow of drug controlled. As shown, one embodiment can include a cycling process alternating normal skin temperature, followed by cold input of the thermoelectric device. Another embodiment can include a cycling process alternating normal skin temperature, followed by cold, and followed by warm or hot temperature of the thermoelectric device. It should also be understood that the thermoelectric drug device of the present invention can include a plurality of cycling process alternating cold, hot, and normothermic (meaning the device is off or there is a quiet period). It should also be understood that for topical drugs that have an internal target organ (e.g., topically applied hormones), a thermoelectric device can apply heat to expedite absorption of the drug by systemic circulation, such as by increasing flow in blood vessels 1502 and 1516.

Figure 5:
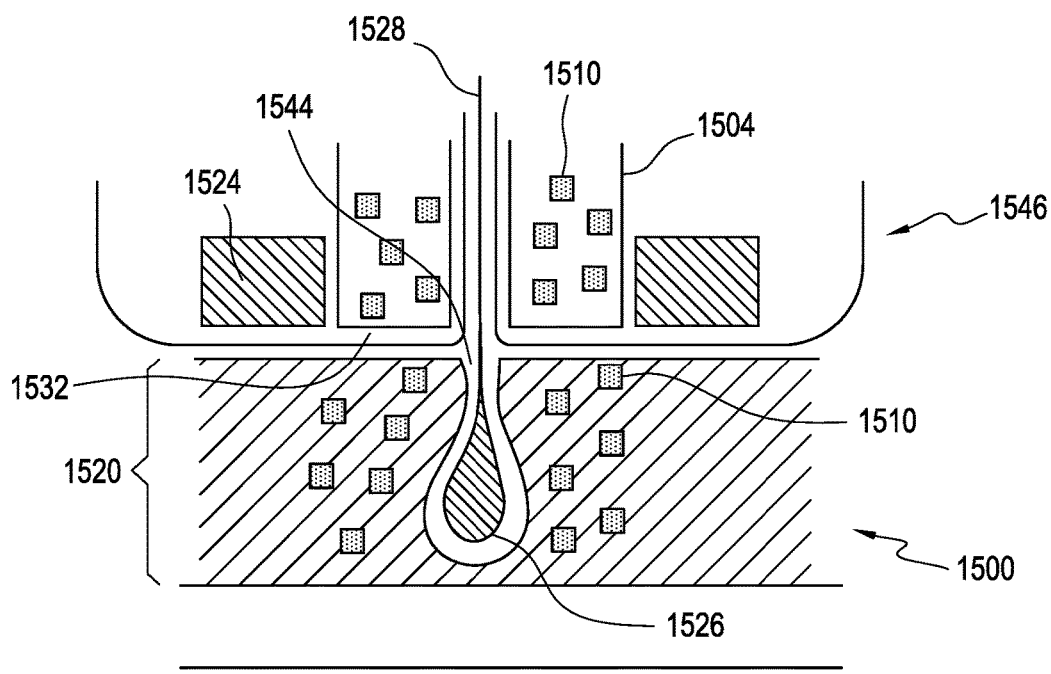
FIG. 5 is a view of skin including a hair follicle with application of heat and drugs in accordance with an exemplary embodiment of the present disclosure.

FIG. 5 shows a schematic cross-sectional view of skin 1500 at the level of a hair follicle 1526 showing hair 1528 exiting through an opening 1544 in skin 1500, wherein a thermoelectric drug device 1546 rests against skin 1500. After about 5 to 10 minutes of contact of an inner surface 1532 of thermoelectric drug device 1546 to surface 1534 of skin 1500, thermoelectric device(s) 1524 are activated, causing heat to be removed or cold to be applied to surface 1534 of skin 1500. Reservoir 1504 contains a hair growth product, and by way of illustration, but not of limitation, includes for example Minoxidil.

Figure 6:
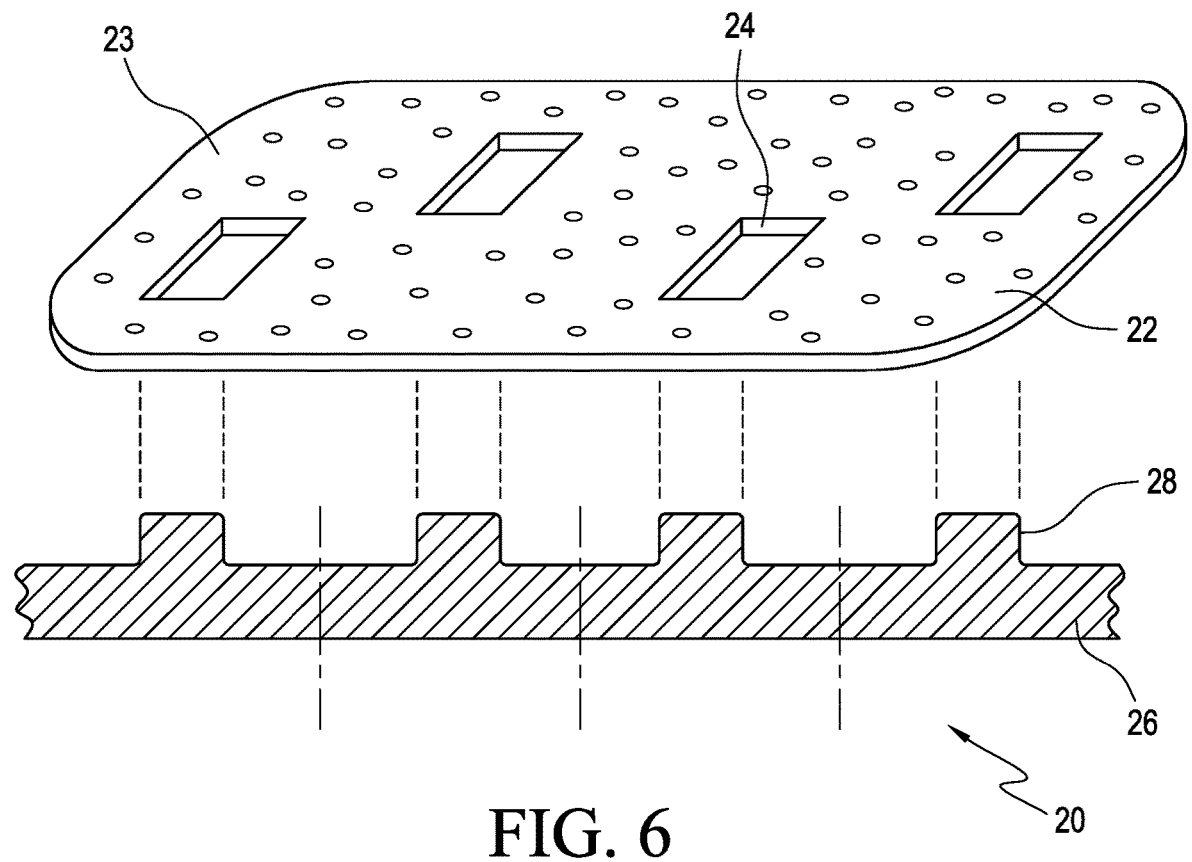
FIG. 6 is a view of a device for skin treatment in accordance with an exemplary embodiment of the present disclosure.
Figure 7:
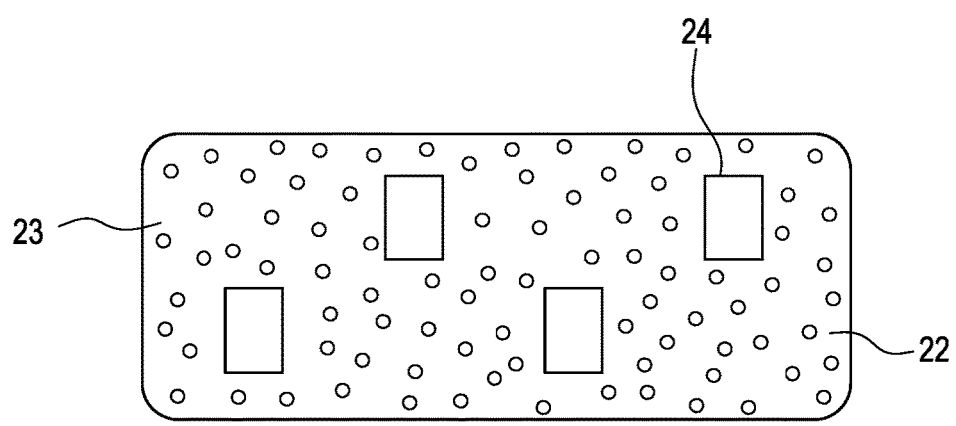
FIG. 7 is a view of a drug application layer in accordance with an exemplary embodiment of the present disclosure.

FIGS. 6 and 7 are views of a device for skin treatment in accordance with an exemplary embodiment of the present disclosure, indicated generally at 20. Device 20 includes a drug application layer 22, which includes a plurality of openings 24 and an exterior surface 23, and a gel layer 26 including a plurality of protrusions 28 configured to extend through openings 24. Device 20 is applied to skin 1500 such that exterior surface 23 of drug application layer 22 contacts skin 1500. Gel layer 26 can be heated or cooled as needed, and the contact of protrusions 28 with skin 1500 applies heat to skin 1500 or removes heat from skin 1500. Gel layer 26 can include any thermally retentive material, which can be heated or cooled as needed for drug permeation and flow through the skin.

Figure 8:
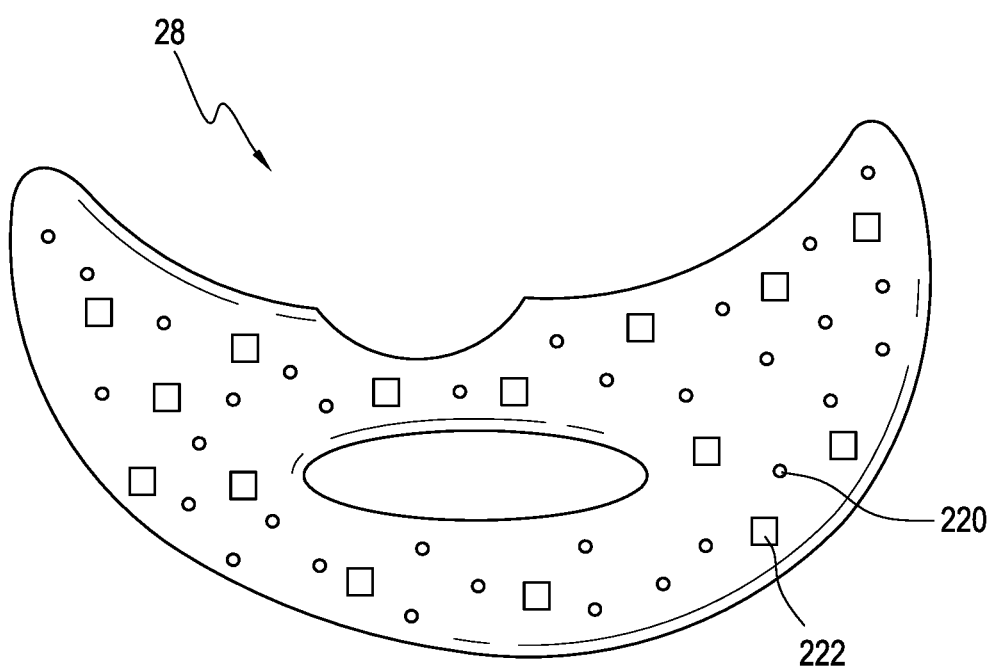
FIG. 8 is a view of a device for skin treatment in accordance with an exemplary embodiment of the present disclosure.

FIG. 8 is a view of a device for skin treatment in accordance with an exemplary embodiment of the present disclosure, indicated generally at 30. Device 30 is configured to include layers disclosed herein for skin treatment, such layers including, for example, a drug application layer, such as drug application layer 22, and a heating and/or cooling portion, such as gel layer 26 or a thermoelectric device. To implement skin treatment, device 30 is pressed against skin 1500, for example, skin 1500 of a face. A drug 220 is then transferred to skin 1500 at a rate that is controlled a plurality of thermoelectric devices 222. Skin treatment device 30 can be used to transfer drug 220 to a lower portion of a face to treat localized conditions on the face.

Figure 9:
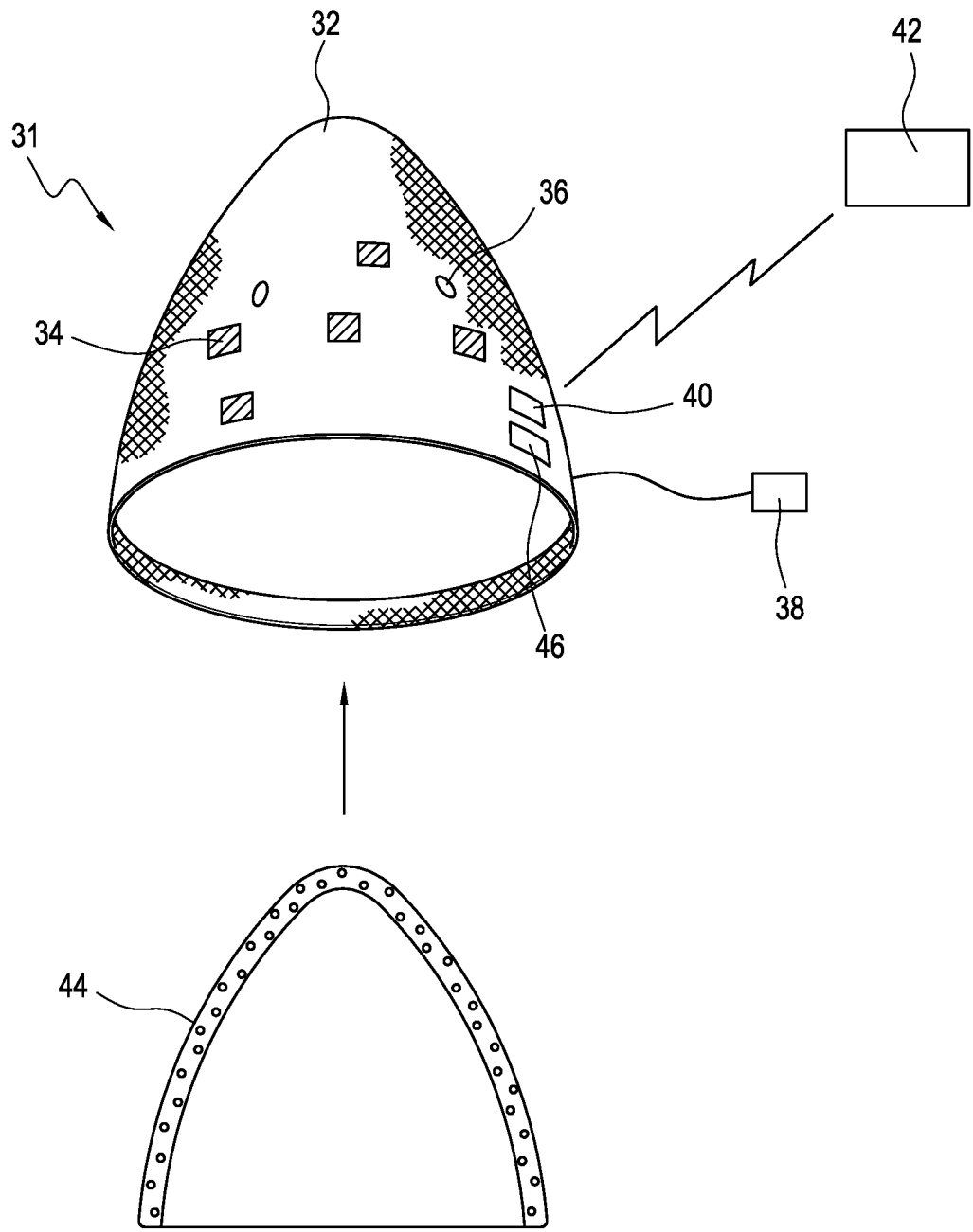
FIG. 9 is a view of another device for skin treatment in accordance with an exemplary embodiment of the present disclosure.

FIG. 9 is a view of another device for skin treatment in accordance with an exemplary embodiment of the present disclosure, indicated generally at 31. Device 31 includes a support 32 in the form of a wearable article such as a hat, cap, helmet, or any head-mounted gear, that includes a plurality of thermoelectric devices 34, one or more temperature sensors 36, a power source 38, a transceiver or receiver 40 for connection to a separate electronic device 42, such as a cell phone, and a removably attached liner 44 configured to include a drug. Separate electronic device 42 can transmit signals to device 31 to control the temperature of thermoelectric devices 34, and thus the rate of drug delivery to skin 1500, and can receive information about the operation of device 31, such as the temperature from one or more temperature sensors 36. Device 31 can also include an integral processor or controller 46, as well as associated elements, such as non-transitory memory. Thermoelectric devices 34 apply heat or cold to skin 1500 to increase or decrease drug permeation and flow through skin 1500.

Figure 10:
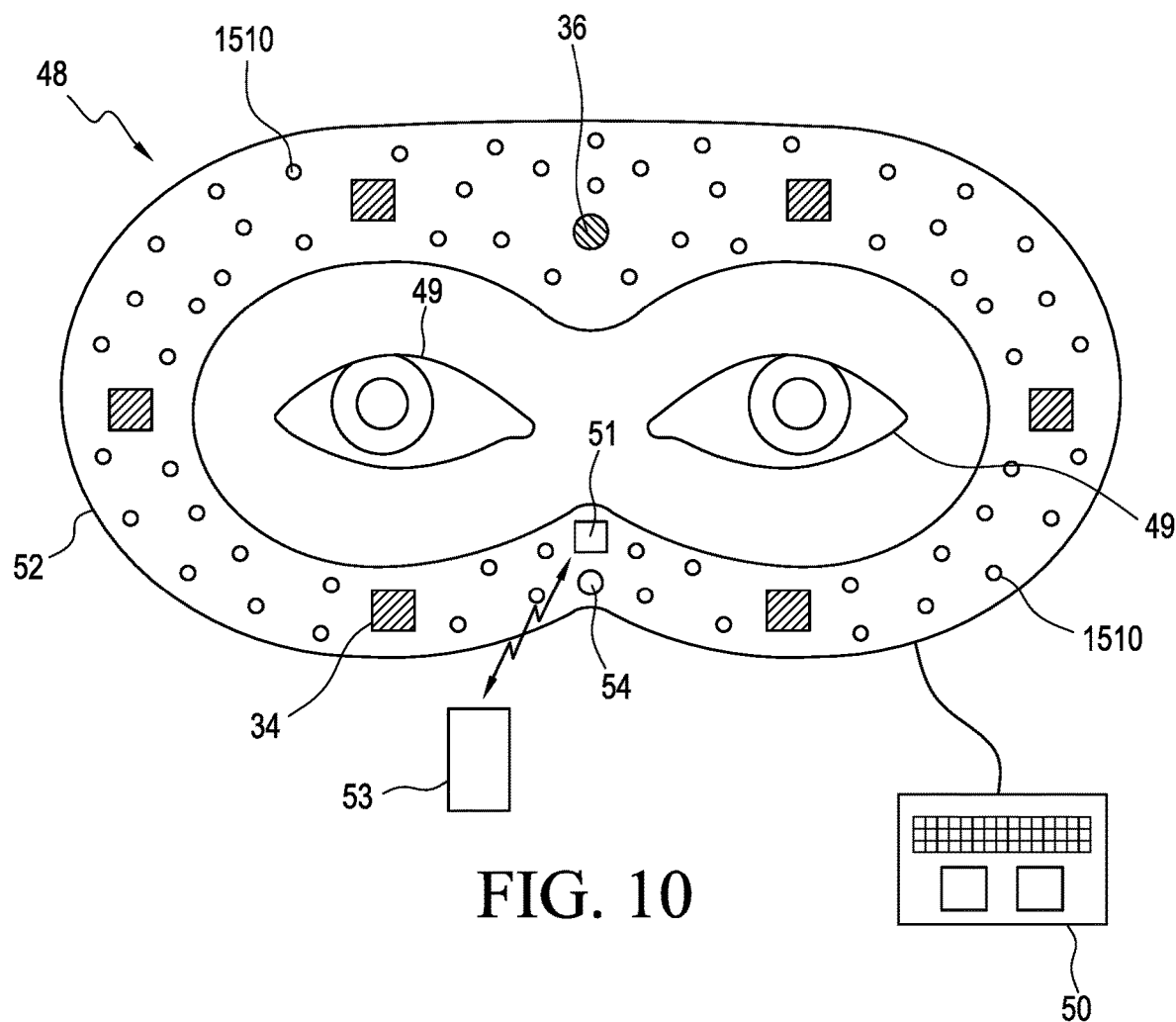
FIG. 10 is a view of yet another device for skin treatment in accordance with an exemplary embodiment of the present disclosure.

FIG. 10 is a view of yet another device for skin treatment in accordance with an exemplary embodiment of the present disclosure, indicated generally at 48. Device 48 is configured as a mask for treatment of skin 1500 around eyes 49. Skin treatment device 48 includes thermoelectric devices 34, at least one temperature sensor 36, a controller or processor 50, a drug layer 52 that includes a drug 53, and an LED 54 for indicating an end of treatment. Processor 50 or skin treatment device 48 can be configured to include a speaker. Skin treatment device 48 can further include a transmitter, receiver, or transceiver 51 configured to communicate with a separate electronic device 53, such as a cell phone, laptop, watch, etc.

FIG. 11 is a view of a further device for skin treatment in accordance with an exemplary embodiment of the present disclosure, indicated generally at 56. Skin treatment device 56 is configured as a circular band with an open area for application to portions of a body suitable for a band, such as an arm, leg, finger, neck, and the like. Device 56 includes a support 58 on which is positioned a drug layer 60, at least one thermoelectric device 62, a power supply 64, and temperature sensors 36. Device 56 also includes a controller or processor 63 and can include a transceiver, LED, speaker 65, etc.

Figure 12:
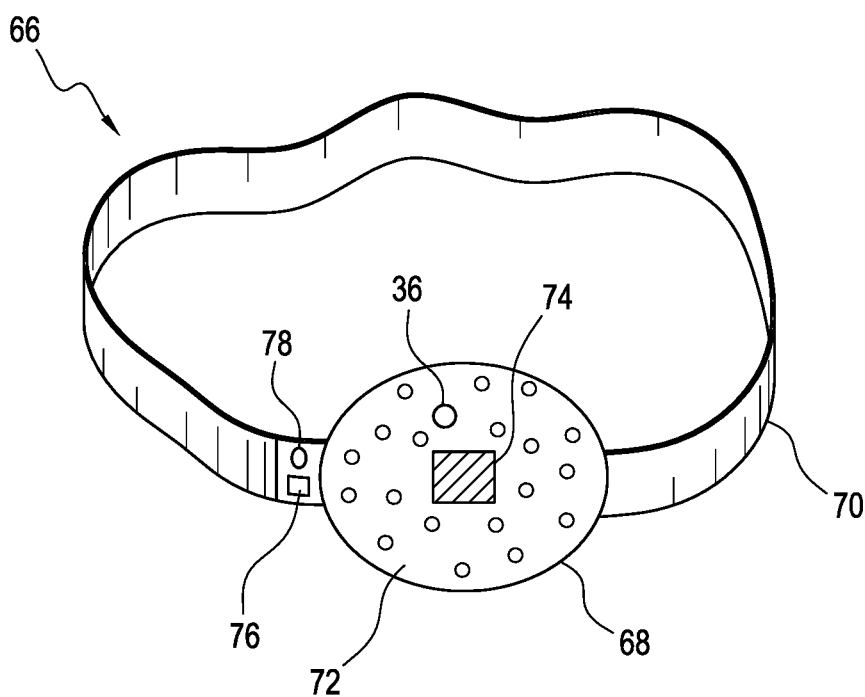
FIG. 12 is a view of yet a further device for skin treatment in accordance with an exemplary embodiment of the present disclosure.

FIG. 12 is a view of yet a further device for skin treatment in accordance with an exemplary embodiment of the present disclosure, indicated generally at 66. Skin treatment device 66 includes a support 68 and a strap 70 configured to secure device 66 to a body, a drug layer 72, a thermoelectric device 74, temperature sensor 36, power supply 76, and controller or Processor 78. Device 66 can also include a transceiver, LED, etc. It should be understood that the strap can include a fastener such as hook and loop (e.g., Velcro) to fasten device 66 to a body part of a human or animals. It should also be understood that device 66 can comprise of only three parts, a drug layer 72, a thermoelectric device 74 with a power source, and a fastener.

FIGS. 13A, 13B, 14, and 15 are views of a device for skin treatment in accordance with an exemplary embodiment of the present disclosure, indicated generally at 80. Such skin may be the skin of a face 83. Skin treatment device 80 includes a support 82, which includes an adhesive layer 81 for attachment to surface 1534 of skin 1500, a drug layer 84 containing a drug, a thermoelectric device 86, a power supply 88, and other electronics 90, such as a transceiver, controller, etc. It should be understood that to minimize the electronics or number of parts in 80 being placed on skin 1500, device 80 can include only drug layer 84 and thermoelectric device 86. This simpler configuration can be applied to any embodiment of the present invention.

Figure 13A:
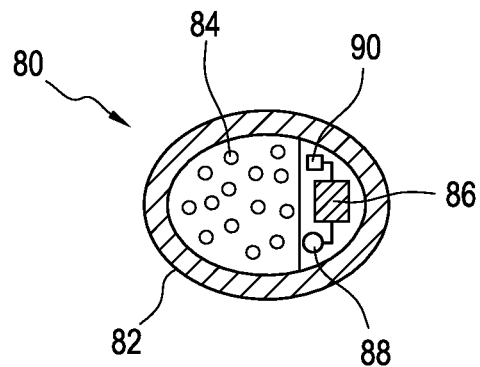
FIG. 13A is a stylized view of a device for skin treatment in accordance with an exemplary embodiment of the present disclosure showing internal elements of the device.
Figure 13B:
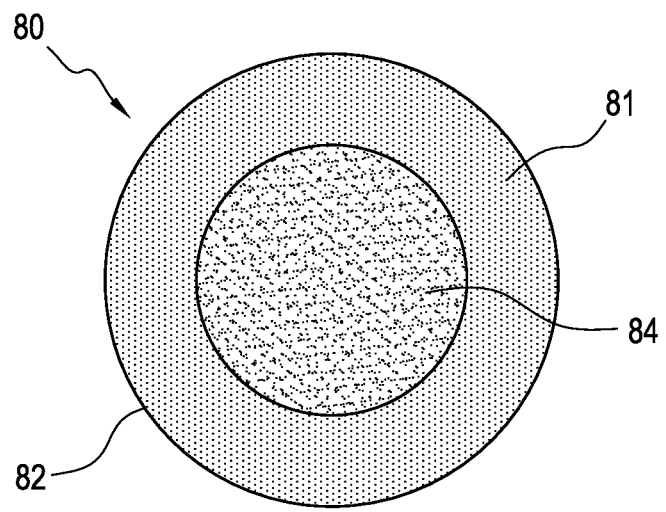
FIG. 13B is bottom view of the device of FIG. 13A.
Figure 13C:
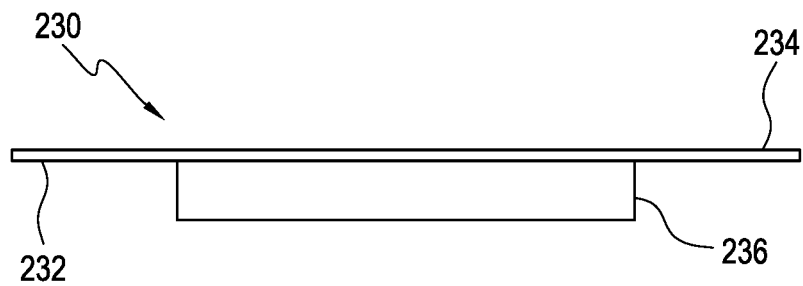
FIG. 13C is a side view of a device for skin treatment in accordance with another exemplary embodiment of the present disclosure.
Figure 13D:
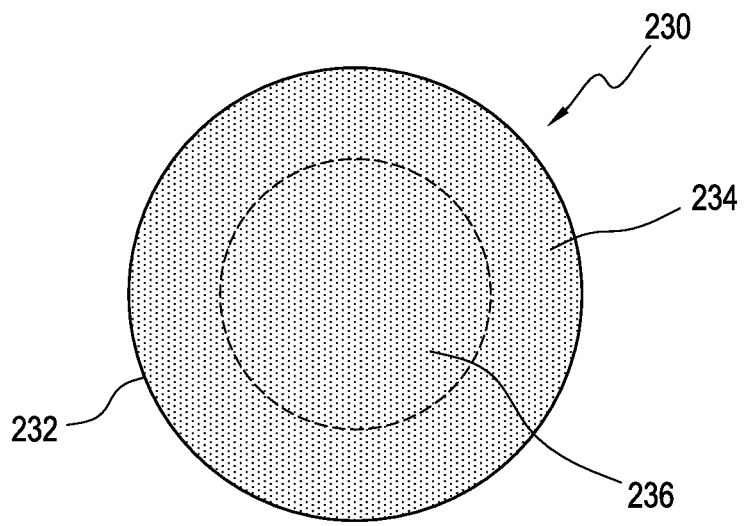
FIG. 13D is a bottom view of the device of FIG. 13C.

Device 80 does not include adhesive in the area of drug layer 84, as can be seen in FIG. 13B. In another embodiment, shown in FIGS. 13C and 13D, a skin treatment device, indicated generally at 230, includes a drug layer or reservoir 236, a support layer or portion 232, and an adhesive layer 234 that extends entirely across drug layer 236. Thus, in this embodiment, drugs from drug layer 84 are transported through adhesive layer 234 to reach skin 1500.

Figure 16:
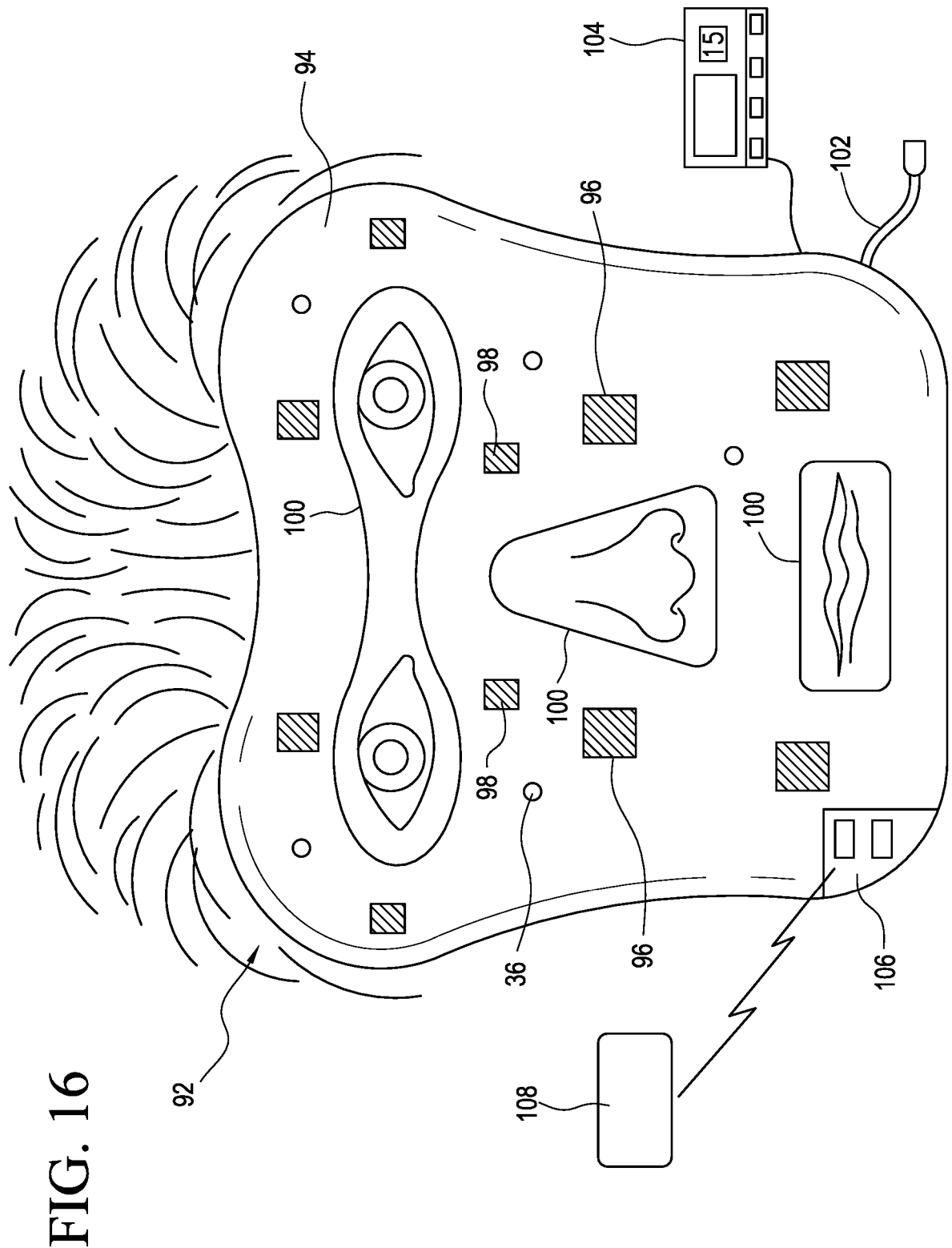
FIG. 16 is a view of another device for skin treatment in accordance with an exemplary embodiment of the present disclosure.

FIG. 16 is a view of another device for skin treatment in accordance with an exemplary embodiment of the present disclosure, indicated generally at 92. Device 92 is in the form of a face mask that is secured to the face by, for example, straps (not shown). Device 92 includes a support 94, thermoelectric devices 96 and 98, temperature sensors 36, openings 100 for various body portions such as eyes, nose, and mouth, a power source 102, a controller or processor 104, and other electronics 106, which may include a transceiver for communication with a separate electronic device 108, etc. It should be understood that to minimize electronics or the number of parts in device 92 being placed on the skin 1500, device 92 can include only a wireless device (e.g., a transceiver, receiver, or transmitter) and electronics can be contained in a remote device. This simpler configuration can be applied to any embodiment of the present invention.

Figure 35:
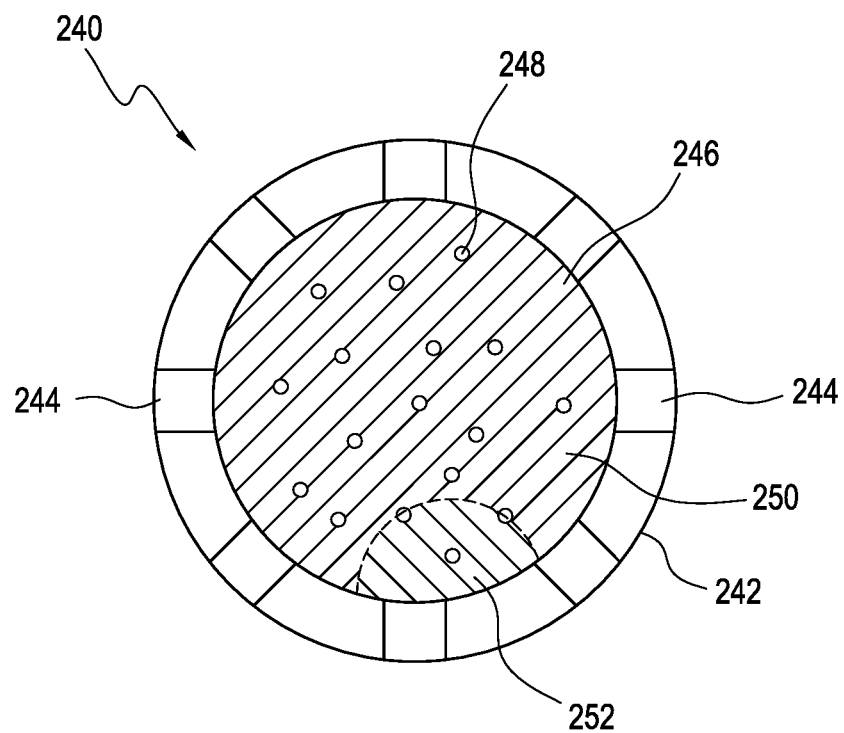
FIG. 35 is a view of a skin treatment device in accordance with an exemplary embodiment of the present disclosure.

FIG. 35 is a view of a skin treatment device, shown generally at 240, in accordance with an exemplary embodiment of the present disclosure. Device 240 includes a support portion 242, on which are positioned a plurality of thermoelectric devices 244 and a drug layer or reservoir 246 that contains a drug 248. Thermoelectric devices 244 are individually controllable to create a cool or cold zone 250 and a warm zone 252, which thus cause drug transport in zone 252 while limiting or inhibiting drug transport in region 250. The benefit of device 240 is that a larger device can be used to provide a small, controllable amount of drug 248 in a localized portion of skin 1500. In addition, device 240 can permit drug transport in varying portions of a larger area with time by moving the location of warm zone 252 through the control of thermoelectric devices 244.

Figure 36:
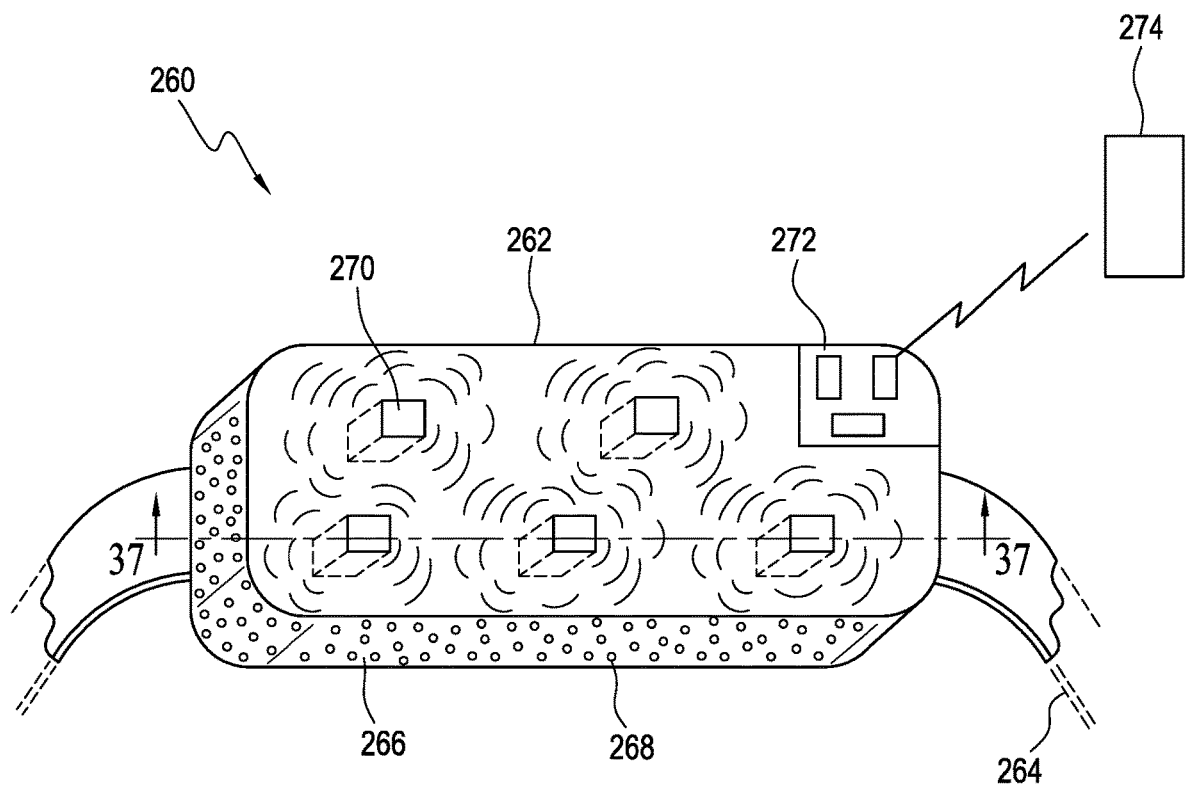
FIG. 36 is a view of a skin treatment device in accordance with an exemplary embodiment of the present disclosure.
Figure 37:
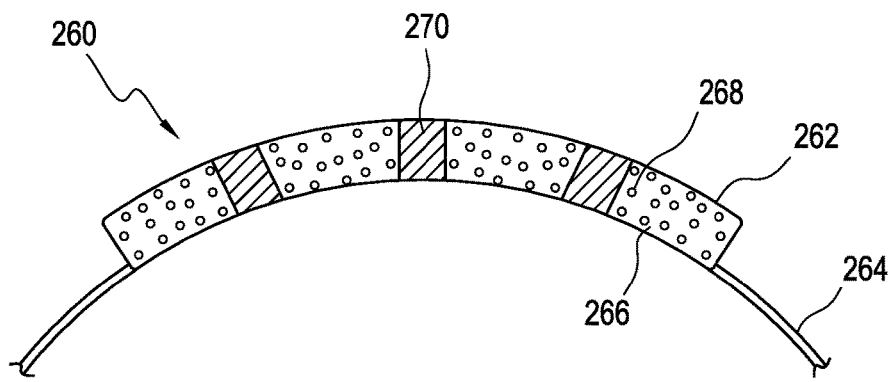
FIG. 37 is a cross-sectional view of the skin treatment device of FIG. 36 along the lines 37-37.

FIGS. 36 and 37 are views of a skin treatment device, indicated generally at 260, in accordance with an exemplary embodiment of the present disclosure. Device 260 includes a body 262 and a strap 264 configured to hold body 262 to a body part, such as a wrist, arm, leg, ankle, etc. Body 262 further includes a drug layer 266 that contains a drug 268, a plurality of thermoelectric devices 270 that operate to modify the temperature of skin 1500 as described elsewhere in this disclosure, and electronics 272, which can include a processor, non-transitory memory, a transceiver for communication with a separate electronic device 274. Body 262 is compliant, flexible, or conformable to curved body parts to provide contact between device 260 and skin 1500. Strap 264 can provide the force or pressure needed to provide contact between body 262 and skin 1500.

Figure 17:
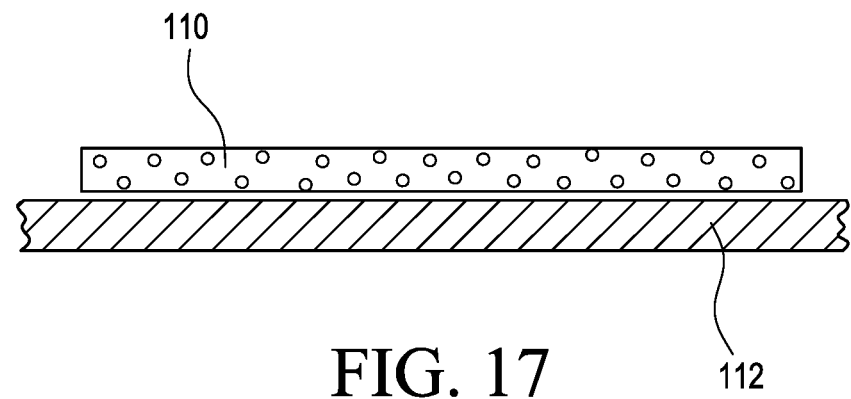
FIG. 17 is a cross-sectional view of layers for application of a skin treatment in accordance with an exemplary embodiment of the present disclosure.

FIG. 17 is a cross-sectional view of layers for application of a skin treatment in accordance with an exemplary embodiment of the present disclosure. Any of the devices shown herein can incorporate this configuration, which includes a drug layer 110 adhered or secured to a gel layer 112. Gel layer 112 can include any thermally retentive material, which can be heated or cooled as needed for drug permeation and flow through the skin. It should be understood that gel layer 112 can be replaced by a thermoelectric device, such as a thermoelectric device 126 shown in FIG. 19. It should be understood that any embodiment can include gel layer 112 and thermoelectric device 126. It should also be understood that thermoelectric device 126 can be replaced by a gel layer, and vice versa.

Figure 18:
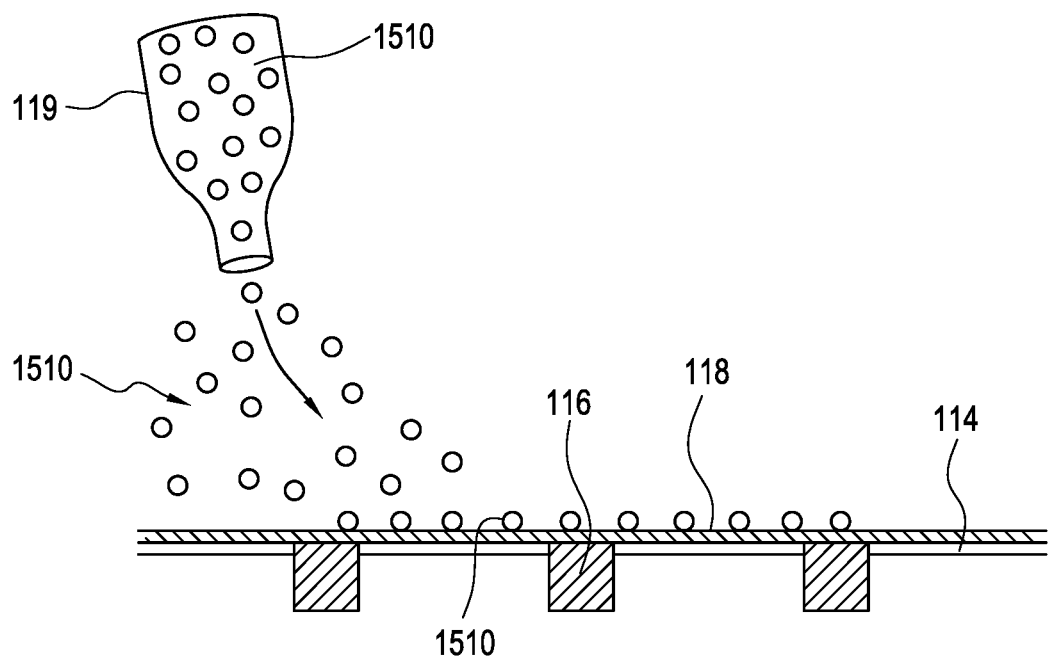
FIG. 18 is a cross-sectional view of layers for application of a skin treatment in accordance with an exemplary embodiment of the present disclosure.

FIG. 18 is a cross-sectional view of layers for application of a skin treatment in accordance with an exemplary embodiment of the present disclosure. In this configuration, which includes a support layer 114 in which are positioned one or more thermoelectric devices 116, and an impermeable barrier layer 118. Drugs can be applied directly to impermeable barrier layer 118 from a drug container 119 before the layers are applied to the skin, where the drugs are immediately accessible to the skin. Drugs can also be applied directly to the skin by rubbing before application of the other elements of the layers. In addition, pressure can be applied against the layers once place on skin 1500.

Figure 19:
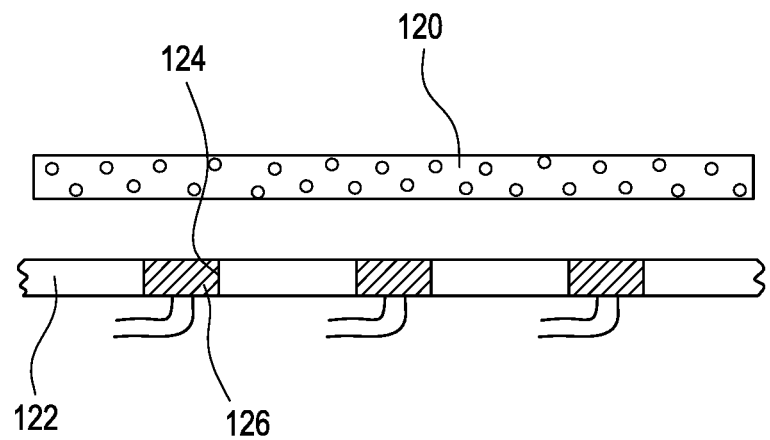
FIG. 19 is a cross-sectional view of layers for application of a skin treatment in accordance with an exemplary embodiment of the present disclosure.

FIG. 19 is a cross-sectional view of layers for application of a skin treatment in accordance with an exemplary embodiment of the present disclosure. Include is a removable drug layer 120, a gel or support layer 122 that includes openings 124 for thermoelectric devices 126. In this embodiment thermoelectric devices 126 do not contact the skin, and thermoelectric devices 126 can apply thermal energy (remove heat or apply heat) directly to drug layer 120, and in this embodiment application of thermal energy to drug layer 120 can be used to activate or inhibit enzymes or to activate drug from an inactive state.

Figure 20:
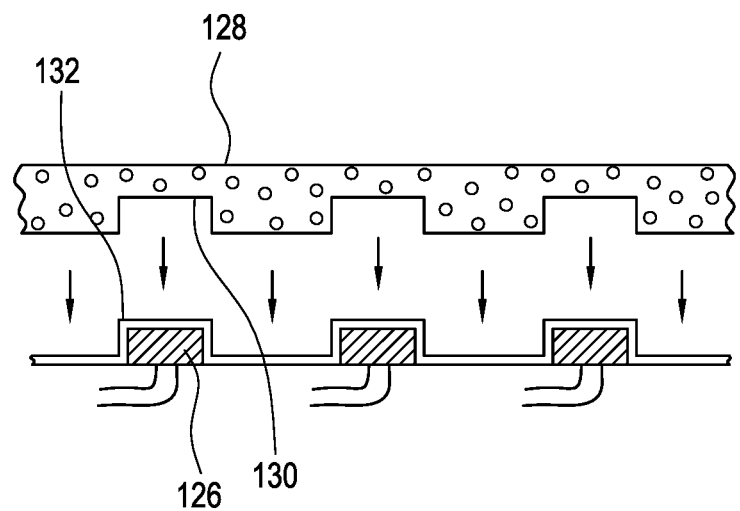
FIG. 20 is a cross-sectional view of layers for application of a skin treatment in accordance with an exemplary embodiment of the present disclosure.

FIG. 20 is a cross-sectional view of layers for application of a skin treatment in accordance with an exemplary embodiment of the present disclosure. Included is a drug layer 128 including recesses 130, thermoelectric devices 126 protruding, and a barrier layer 132 over thermoelectric devices 126. Thermoelectric devices 126 protrude to mate with recesses 130 in drug layer 128. In this embodiment thermoelectric devices 126 do not contact the skin, and thermoelectric devices 126 can apply thermal energy (remove heat or apply heat) to a portion of drug layer 128, and in this embodiment application of thermal energy to drug layer 128 can be used to activate or inhibit enzymes or to activate drug from an inactive state.

Figure 21:
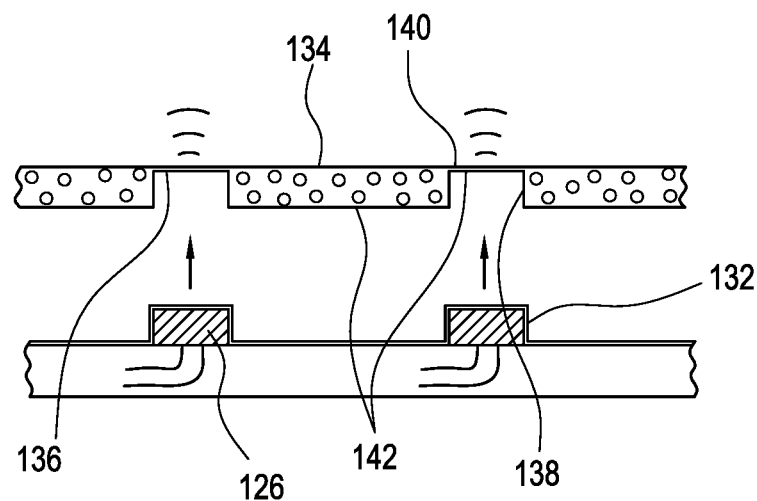
FIG. 21 is a cross-sectional view of layers for application of a skin treatment in accordance with an exemplary embodiment of the present disclosure.

FIG. 21 is a cross-sectional view of layers for application of a skin treatment in accordance with an exemplary embodiment of the present disclosure. This configuration is similar to the configuration of FIG. 20, but a drug layer 134 includes recesses 138 that are covered at an end 140 by a thin, impermeable barrier layer 142, as compared to the configuration of FIG. 20. Heat is removed or applied to the skin via barrier layer 142 positioned at end 140.

Figure 22:
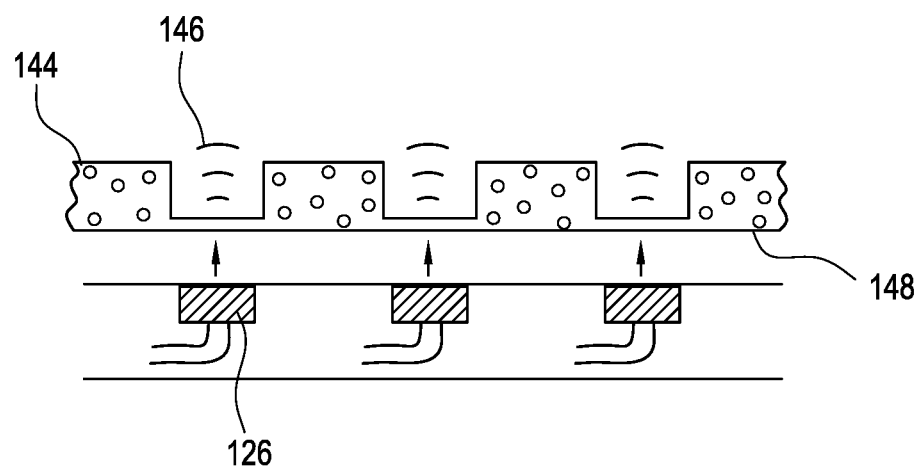
FIG. 22 is a cross-sectional view of layers for application of a skin treatment in accordance with an exemplary embodiment of the present disclosure.

FIG. 22 is a cross-sectional view of layers for application of a skin treatment in accordance with an exemplary embodiment of the present disclosure. This configuration includes a drug layer 144 with recesses 146 that face away from thermoelectric devices 126. An impermeable layer 148 separates drug layer 144 from thermoelectric devices 126.

Figure 23:
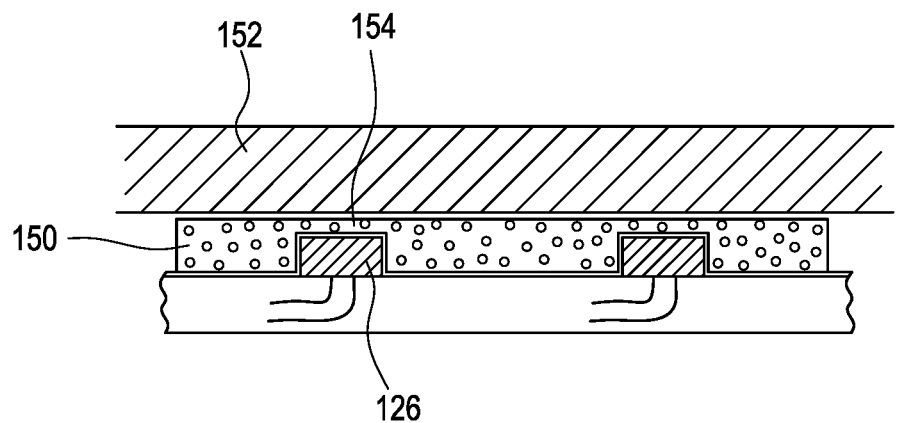
FIG. 23 is a cross-sectional view of layers for application of a skin treatment in accordance with an exemplary embodiment of the present disclosure.

FIG. 23 is a cross-sectional view of layers for application of a skin treatment in accordance with an exemplary embodiment of the present disclosure. These layers are similar to the layers of FIG. 20, with a drug layer 150 positioned adjacent to skin 152, but the thickness of drug layer 150 is less in location 154 than the similar location in FIG. 20.

Figure 24:
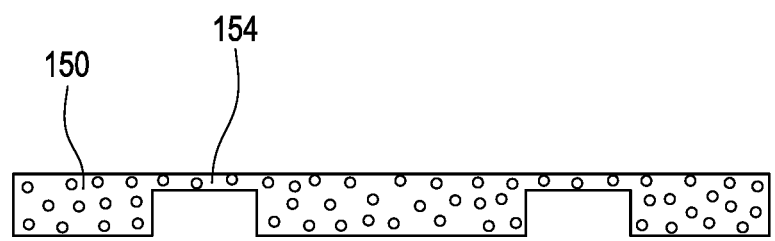
FIG. 24 is a cross-sectional view of a drug application layer in accordance with an exemplary embodiment of the present disclosure.

FIG. 24 is a cross-sectional view of drug application layer 150.

Figure 25:
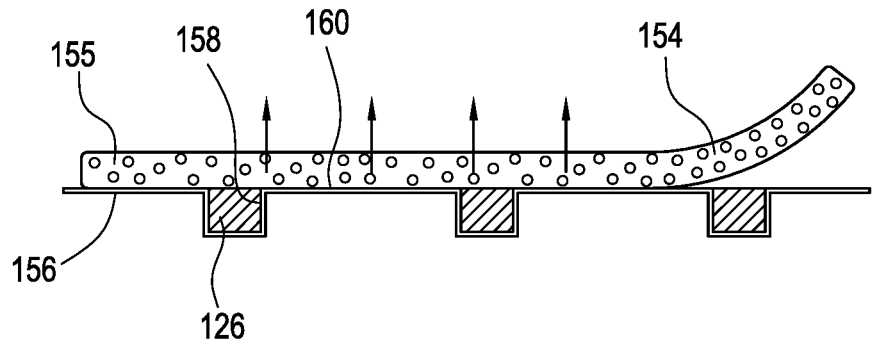
FIG. 25 is a cross-sectional view of layers for application of a skin treatment in accordance with an exemplary embodiment of the present disclosure.

FIG. 25 is a cross-sectional view of a drug application layer in accordance with an exemplary embodiment of the present disclosure. Includes a drug layer 154 adjacent to a support layer 156 with recesses 158 for thermoelectric devices 126 that are flush, even, or the same height as an outer surface 160 of support layer 156. FIG. 25 shows an exemplary embodiment where drug layer 154 is removably attached to support layer 156, and drug layer 154 is shown peeling off from support layer 156.

Figure 26:
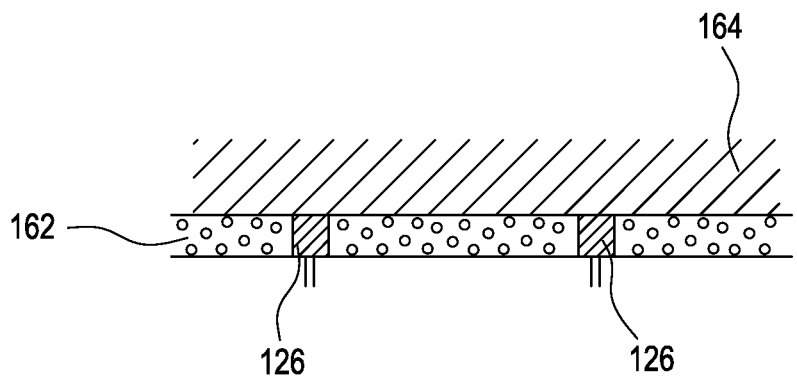
FIG. 26 is a cross-sectional view of layers for application of a skin treatment in accordance with an exemplary embodiment of the present disclosure.

FIG. 26 is a cross-sectional view of layers for application of a skin treatment in accordance with an exemplary embodiment of the present disclosure. Included is a drug layer 162 similar to drug layer 134 of FIG. 21 that permits thermoelectric devices 126 to be positioned nearly in contact with skin 164.

Figure 27:
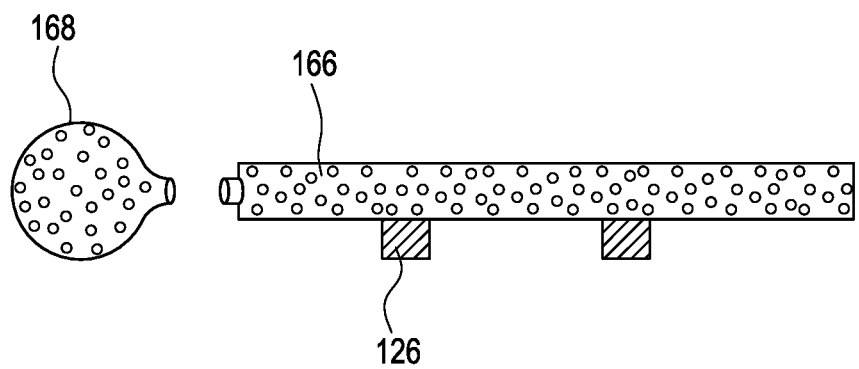
FIG. 27 is a cross-sectional view of layers for application of a skin treatment in accordance with an exemplary embodiment of the present disclosure.

FIG. 27 is a cross-sectional view of layers for application of a skin treatment in accordance with an exemplary embodiment of the present disclosure. Includes a drug layer 166 that can be refilled with a drug supply 168. Drug layer 166 either includes a reservoir or permits drug to flow along its length to allow replenishment of the drug. It should be understood that liner 44 shown in FIG. 9 can function as a drug reservoir and liner 44 can be permanently attached to support 32 and device 31 can be one integral physical unit. It should also be understood that any drug layer of any embodiment in the present invention can function as a drug reservoir and said drug layer can be permanently attached to a support and be one integral physical unit.

Figure 28:
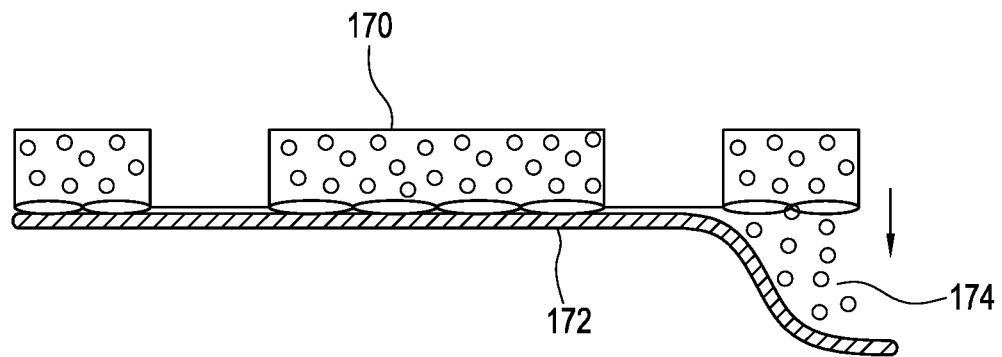
FIG. 28 is a cross-sectional view of layers for application of a skin treatment in accordance with an exemplary embodiment of the present disclosure.

FIG. 28 is a cross-sectional view of layers for application of a skin treatment in accordance with an exemplary embodiment of the present disclosure. Includes a drug layer 170 and a release liner or layer 172. This figure shows that as liner 172 is removed, drugs 174 are allowed to flow from drug layer 170 to be accessible to skin 1500.

Figure 29:
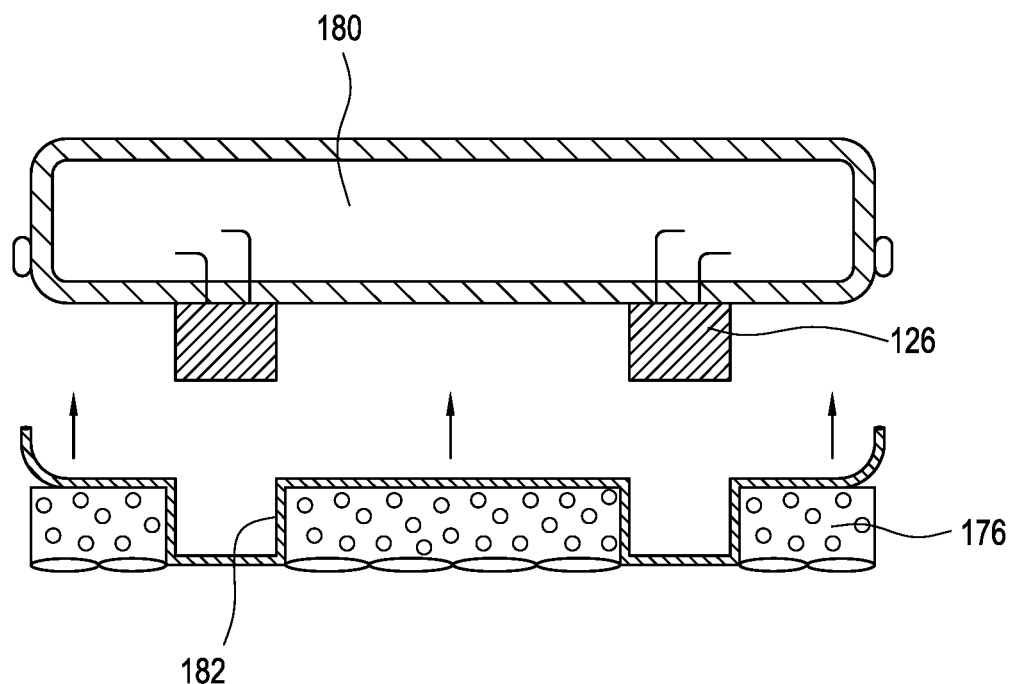
FIG. 29 is a cross-sectional view of layers for application of a skin treatment in accordance with an exemplary embodiment of the present disclosure.
Figure 30:
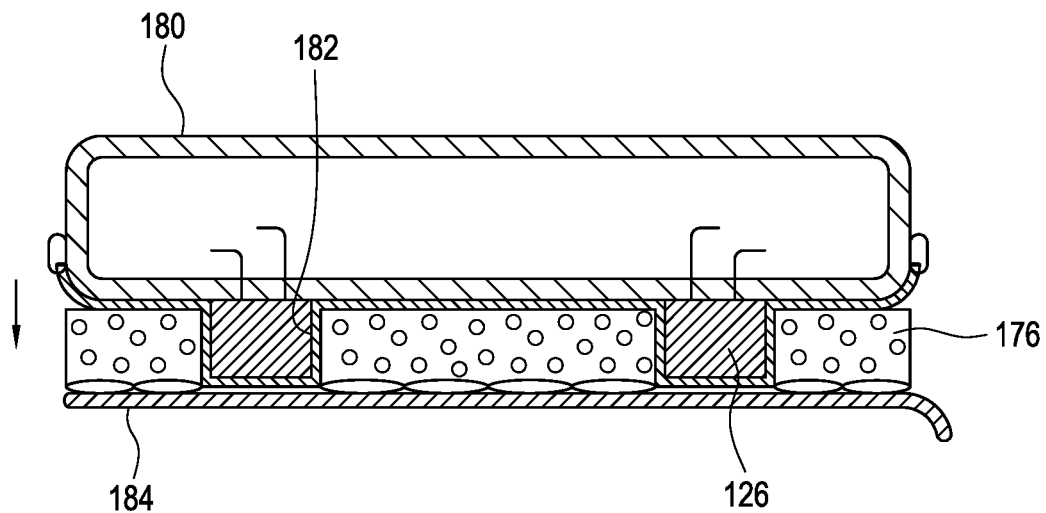
FIG. 30 is a cross-sectional view of layers for application of a skin treatment in accordance with an exemplary embodiment of the present disclosure.

FIGS. 29 and 30 are cross-sectional views of layers for application of a skin treatment in accordance with an exemplary embodiment of the present disclosure. The layers includes a drug layer 176 including recesses 182 to hold thermoelectric devices 126. Thermoelectric devices 126 are supported on an inflatable structure 180 that provides pressure on the skin of a patient to increase drug absorption by the skin. FIG. 30 shows an assembled configuration with a release liner or layer 184.

Figure 31:
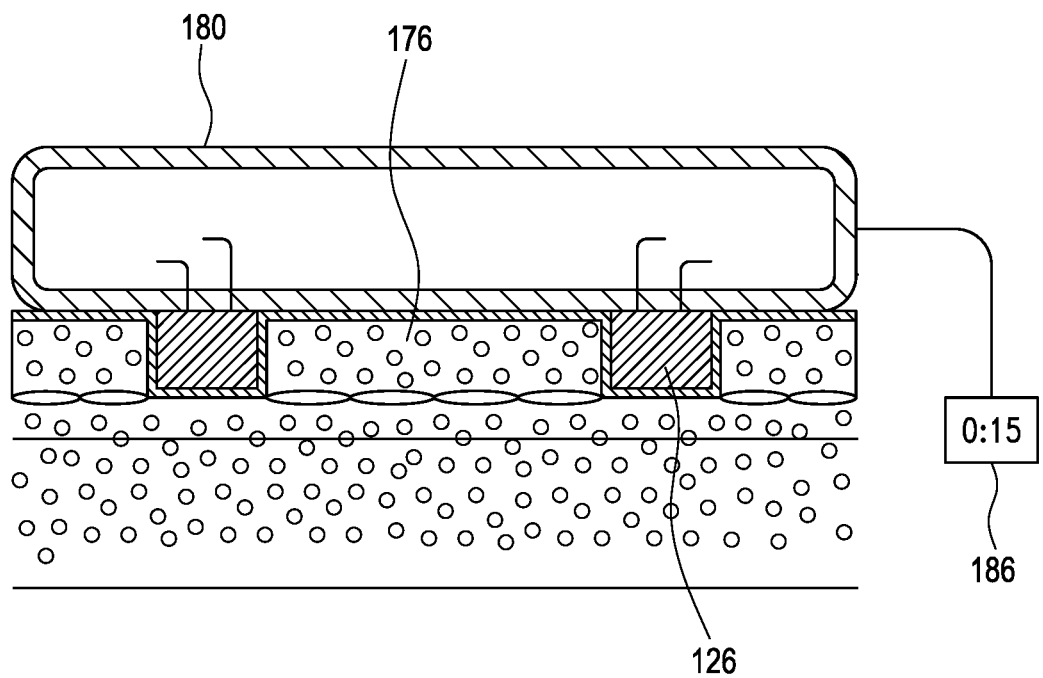
FIG. 31 is a cross-sectional view of layers for application of a skin treatment in accordance with an exemplary embodiment of the present disclosure.

FIG. 31 is a cross-sectional view of layers for application of a skin treatment in accordance with an exemplary embodiment of the present disclosure. This configuration is similar to the configuration of FIGS. 29 and 30, but includes a timer 186 to depressurize inflatable structure 180 automatically when a predetermined treatment time is reached. It should be understood that inflatable structure 180 can be inflated with air, water, a gel, etc.

Figure 32:
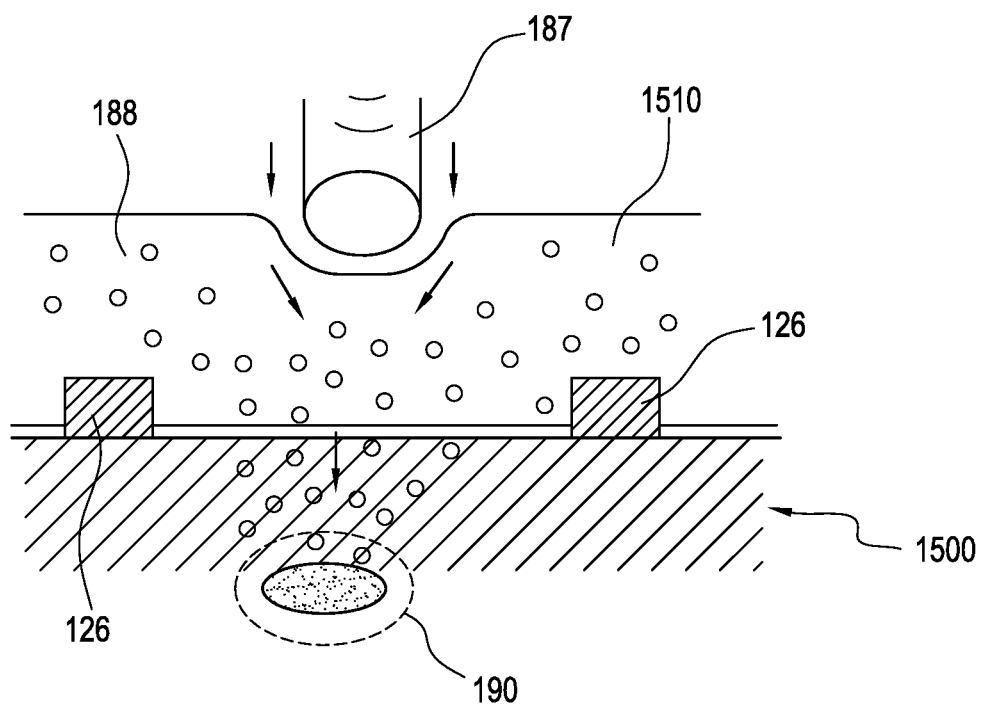
FIG. 32 is a cross-sectional view of layers for application of a skin treatment in accordance with an exemplary embodiment of the present disclosure.

FIG. 32 is a cross-sectional view of layers for application of a skin treatment in accordance with an exemplary embodiment of the present disclosure. Includes a drug layer 188 that is being pressed on by an external object 187, i.e., a finger, to show that pressure on drug layer 188 can be relatively simple, as opposed to straps, supports, and inflatables. Drug layer 188 is treating an abscess 190.

Figure 33:
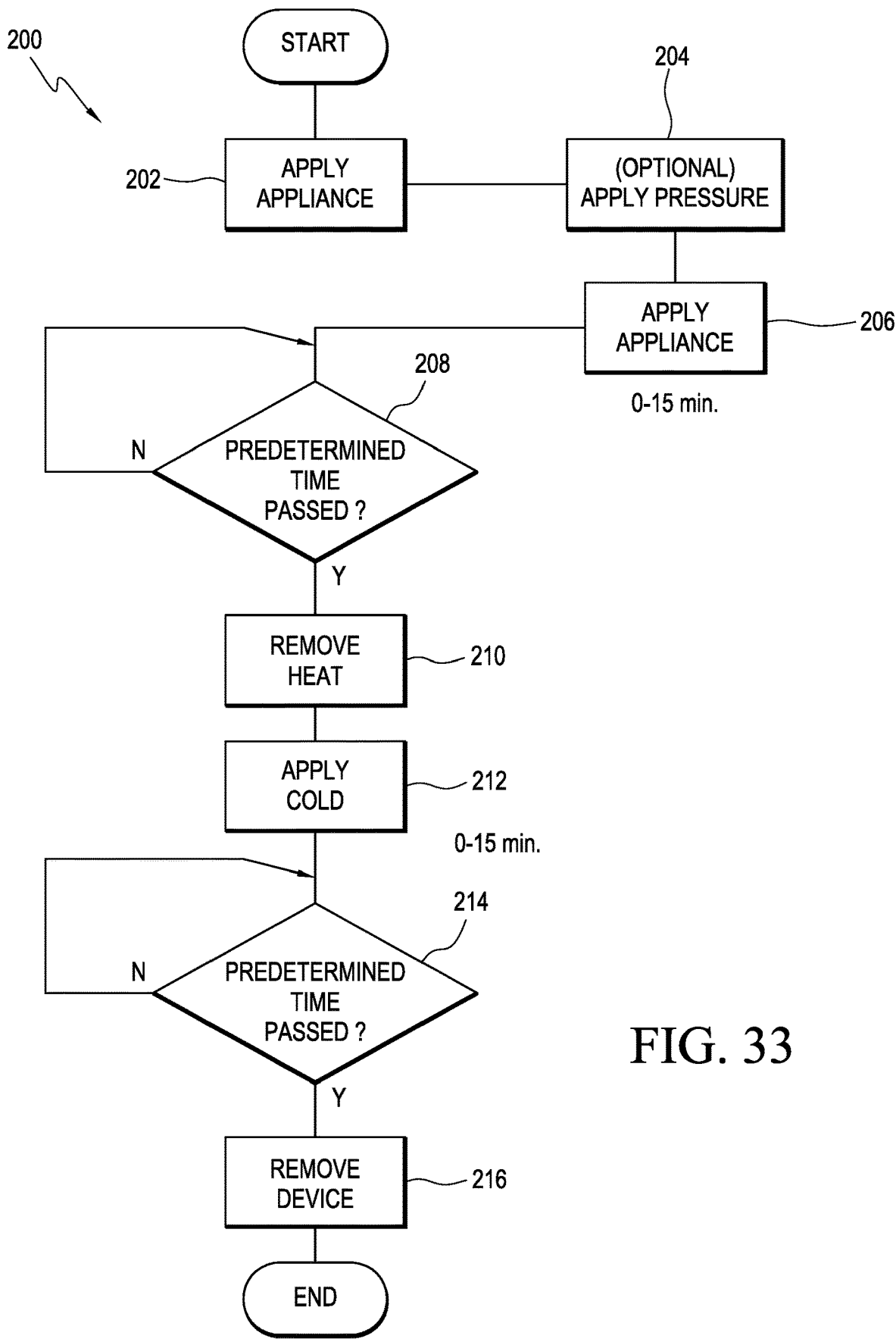
FIG. 33 is a process for application of a skin treatment in accordance with an exemplary embodiment of the present disclosure.

FIG. 33 is a process for application of a skin treatment, indicated generally at 200, in accordance with an exemplary embodiment of the present disclosure. In process 200, a drug layer is applied at a step 202, as a part of a device, and pressure is provided, if available, at a step 204. In many embodiments, heat is then applied at a step 206, though heat is not necessary in all embodiments and cold may be applied instead. Regardless of whether heat is applied, the drug layer will be applied for a predetermined time at a step 208, which can be in the range from more than 0 to 15 minutes, or even longer for some drugs and treatments. If heat was applied, it is then removed at a step 210 after predetermined time step 208. If cold is available, it is applied at a step 212 to remove heat from skin 1500. Alternatively, the length of time the drug is applied can be extended. The cold is applied, or heat is removed, for a predetermined time at a step 214, which can be, for example, 0 to 15 minutes, or even longer for some drugs and treatments, after which the drug layer and or device is removed at a step 216.

Figure 34:
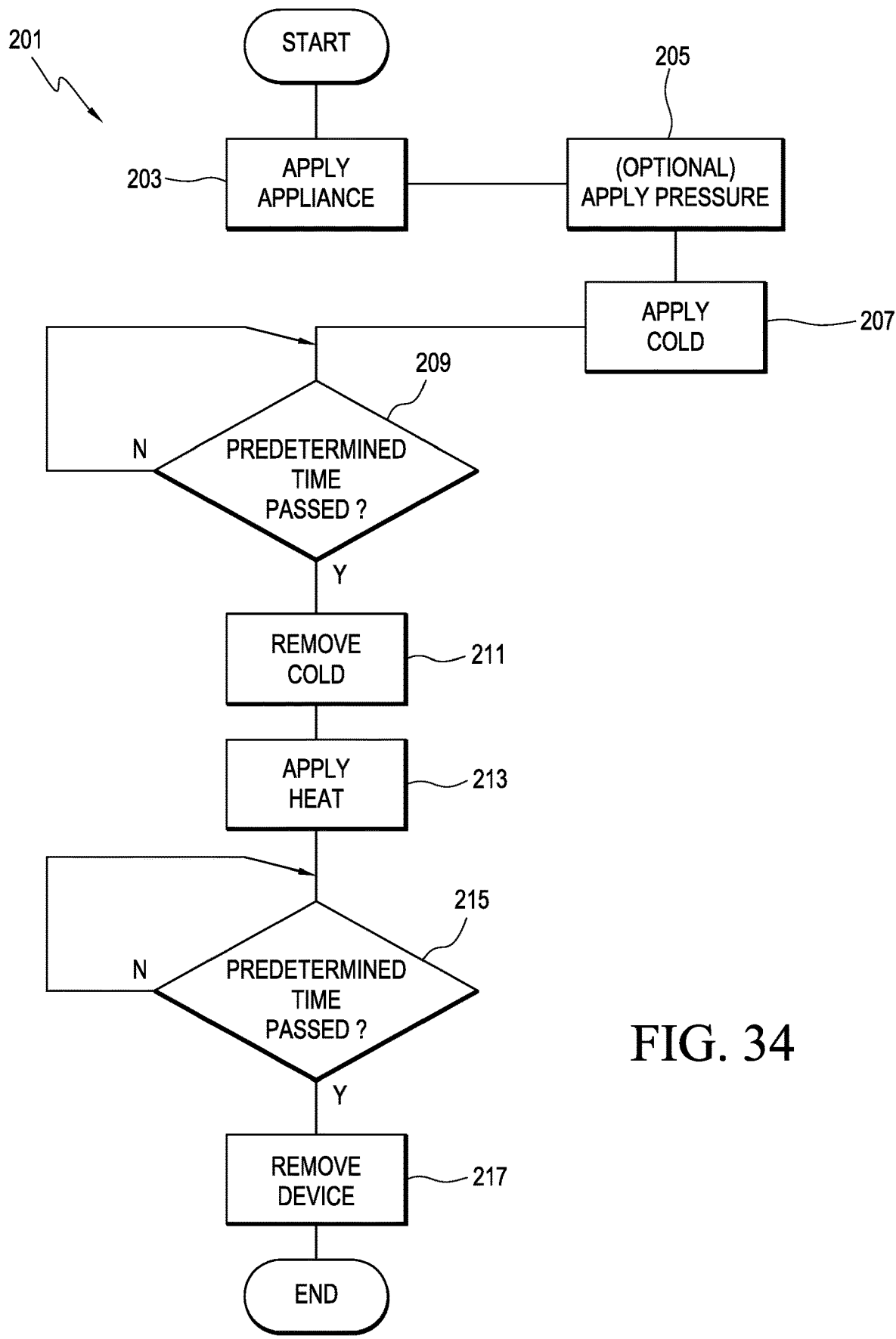
FIG. 34 is another process for application of a skin treatment in accordance with an exemplary embodiment of the present disclosure.

FIG. 34 is another process for application of a skin treatment, indicated generally at 201, in accordance with an exemplary embodiment of the present disclosure. In process 201, a drug layer is applied at a step 203, as a part of a device, and pressure is provided, if available, at a step 205. In many embodiments, heat is then removed (cold applied) at a step 207, though cold is not necessary in all embodiments and heat may be applied instead. Regardless of whether heat is removed, the drug layer will be applied for a predetermined time at a step 209, which can be in the range from more than 0 to 15 minutes, or even longer for some drugs and treatments. If heat was removed, it is then applied at a step 211 after predetermined time step 209. If heat is available, it is applied at a step 213 to apply heat to skin 1500. Alternatively, the length of time the drug is applied can be extended. The heat is applied, for a predetermined time at a step 215, which can be, for example, 0 to 15 minutes, or even longer for some drugs and treatments, after which the drug layer and or device is removed at a step 217.

A further initial step may include application of the drug layer, in which the thermoelectric device is off, and during this time the drug is being absorbed by the skin by diffusion. After a predetermined time the thermoelectric device is activated and heat is removed or applied, and then the process can continue with the remaining steps described herein.

A preferred time between any thermoelectric device being off and the thermoelectric being activated is equal to or less than 60 min, is more preferably equal to or less than 30 min, is even more preferably equal to or less than 15 min, is yet more preferably equal to or less than 10 min, and is most preferably equal to or less than 5 min. The time is dependent on the type of drug and type of treatment.

The preferred time between application of heat and removal of heat by the thermoelectric device is equal to or less than 30 min, is more preferably equal to or less than 15 min, is even more preferably equal to or less than 7.5 min, is yet more preferably equal to or less than 5 min, and is most preferably equal to or less than 2.5 min. The time is dependent on the type of drug and type of treatment.

A preferred time between removal of heat and application of heat by the thermoelectric device is equal to or less than 30 min, is more preferably equal to or less than 15 min, is even more preferably equal to or less than 7.5 min, is yet more preferably equal to or less than 5 min, and is most preferably equal to or less than 2.5 min. The time is dependent on the type of drug and type of treatment.

The application of heat increases skin permeability and the rate of drug flow through the layers of the skin. The predetermined time permits the drug to flow through at least the epidermis and the dermis, and in some cases the subcutaneous layer. A pooling effect is achieved in the dermis during the predetermined time. Application of cold, decreases permeation and drug flow, causing the drug in the epidermis to dwell longer than it would without the application of cold. Thus, the benefit of the present disclosure, is to increase the length of time a drug is present in one or more layers of skin to achieve a therapeutic effect.

Figure 38:
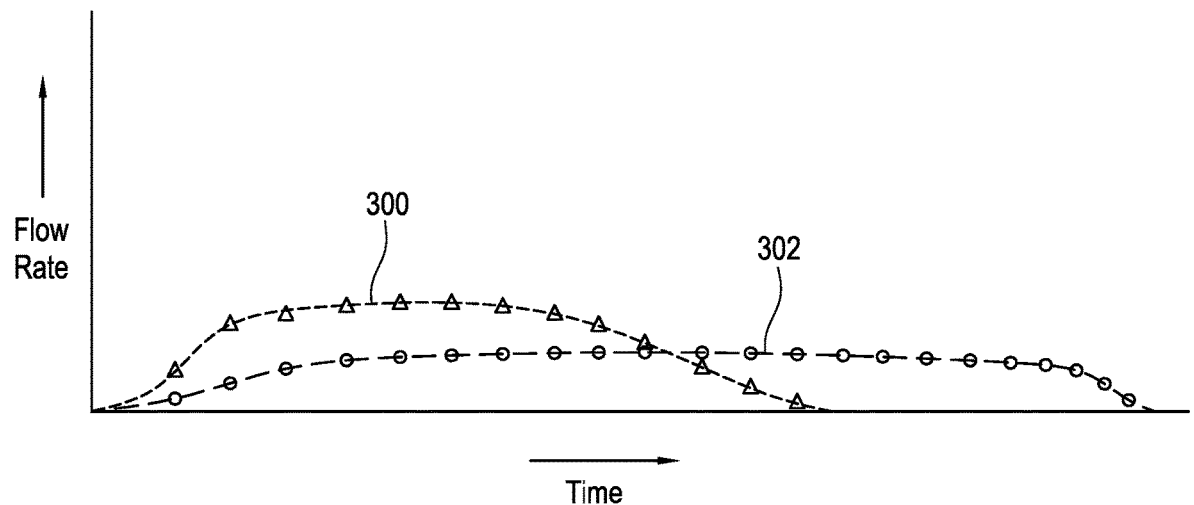
FIG. 38 is a graph showing drug flow by removal of heat or application of cold in accordance with an exemplary embodiment of the present disclosure.
Figure 39:
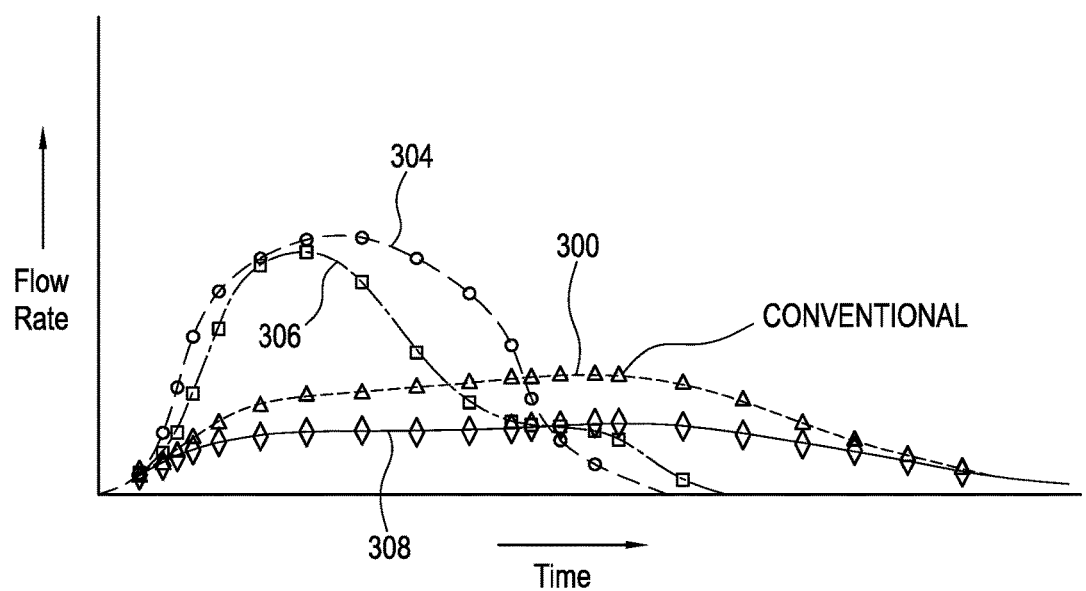
FIG. 39 is a graph showing drug flow by modification of skin temperature in accordance with an exemplary embodiment of the present disclosure.

FIGS. 38 and 39 show graphs of drug flow rate into blood vessels as modified by the application of the principles described herein. A drug flow rate over time is shown as line 300. The flow rate is non-controllable and relies on the presence of a drug at an interface between a device and skin. As the amount of drug in the device decreases, the flow rate decrease, as can be seen in FIGS. 38 and 39.

As shown in FIG. 38, by controlled application of cooling or removal of heat to skin 1500, the rate of drug flow into blood vessels, such as major blood vessel 1502, is decreased, and the length of time during which drug flows into blood vessels is increased.

In addition to application of cooling or removal of heat, heat can be applied to skin 1500 to increase the rate of drug flow. As should be understood, the ability to control the flow of drugs into blood vessels leads to significant improvements in the capability to control drug flow into a body without use of needles or other such invasive devices. Line 304 shows an application of heat to skin 1500, increasing the rate of drug flow over a conventional drug patch. Such increased rate of drug flow can be important in clinical applications where speed of delivery is important, such as treating an active heart condition or an active chemical imbalance, including hormonal, insulin, enzymes, etc. In addition, line 306 shows a drug delivery profile that initially provides a relatively high flow rate, followed by a flow rate that is less than that of a conventional drug patch, followed by a tapered shut off of drug flow. Line 308 is another controlled drug release that terminates at a time that is less than that of line 302 in FIG. 38, showing another aspect of the controllability of drug flow using the devices of the present disclosure.

While thermoelectric device is used herein, it should be understood that other devices can be used, such as a resistive heater, a chemical heater or cooler, etc. It should be understood that the drug layers are layers of absorbent material that capture a drug, but which readily permits the drug to pass from the material to skin for absorption. It should be understood that the features of each of the layer embodiments are compatible with each of the disclosed devices, and features from each of the layer arrangements, such as the inflatable portion, are adaptable to any layer configuration. It should be understood that any part of any embodiment can be combined to form one single embodiment, and that various embodiments can be combined to form one single embodiment. It should be understood that embodiments can be applied to humans or animals, and to any biological surface including skin and mucosal surfaces. It should be understood that embodiments can include an additional layer or part comprised of drug permeation enhancer, and/or water, and/or chemical compounds such as vasodilators or vasoconstrictors. It should be understood that any embodiment showing as two or more separate parts can be combined in one physical unit.

While various embodiments of the disclosure have been shown and described, it is understood that these embodiments are not limited thereto. The embodiments may be changed, modified, and further applied by those skilled in the art. Therefore, these embodiments are not limited to the detail shown and described previously, but also include all such changes and modifications.

I claim:

1. A method of controlling drug delivery to skin, the method comprising:
   removing heat from the skin;
   applying a drug to an external surface of the skin while simultaneously removing heat from the skin for a predetermined period to permit the drug to flow through the external surface to build up in a pool in a superficial skin layer; and
   permitting the pooled drug to flow to a vasoconstricted blood vessel located in the superficial skin layer at a flow rate less than a flow rate when the skin is at a normal body temperature by controlling a temperature of the skin at a temperature less than the normal body temperature during the removal of the heat from the skin; wherein the heat is removed at a first location on the skin, and the drug is applied at a second location on the skin;
   wherein the drug is applied to the skin about a periphery of the first location; or wherein the heat is removed about a periphery of the second location.

2. The method of claim 1, further including providing heat to the skin prior to removing heat from the skin to increase drug flow to the superficial skin layer.

3. The method of claim 2, wherein heat is applied to the skin for a predetermined interval greater than 0 minutes and less than 15 minutes.

4. The method of claim 1, wherein the heat is removed for a predetermined interval greater than 0 minutes and less than 15 minutes.

5. The method of claim 1, wherein the heat is removed by a thermoelectric device.

6. The method of claim 1, wherein the heat is removed by a cooled gel material.

7. The method of claim 1, wherein the drug is applied at the first location on the skin.

8. A method of controlling drug delivery to skin, the method comprising:
   positioning a device on the skin that is configured to provide vasoconstriction of blood vessels through cooling and to simultaneously provide drug delivery to an external surface of the cooled skin;
   cooling the skin to cause vasoconstriction while simultaneously delivering a drug to the external surface of the skin to permit the drug to build up in a pool in a superficial skin layer; and
   permitting the pooled drug to flow to a vasoconstricted blood vessel located in the superficial skin layer at a flow rate less than a flow rate when the skin is at a normal body temperature by controlling a temperature of the skin at a temperature less than the normal body temperature during the cooling of the skin; wherein the skin is cooled at a first location on the skin, and the drug is applied at a second location on the skin;
   wherein the drug is applied to the skin about a periphery of the first location; or wherein the skin is cooled about a periphery of the second location.

9. The method of claim 8, further including providing heat to the skin prior to cooling the skin to increase drug flow to the superficial skin layer.

10. The method of claim 9, wherein heat is applied to the skin for a predetermined interval greater than 0 minutes and less than 15 minutes.

11. The method of claim 8, wherein the skin is cooled for a predetermined interval greater than 0 minutes and less than 15 minutes.

12. The method of claim 8, wherein cooling is provided by a thermoelectric device.

13. The method of claim 8, wherein cooling is provided by a cooled gel material.

\* \* \* \* \*